US008979753B2

(12) United States Patent
Corsetti et al.

(10) Patent No.: US 8,979,753 B2
(45) Date of Patent: Mar. 17, 2015

(54) IDENTIFYING RISK OF A MEDICAL EVENT

(75) Inventors: James P. Corsetti, Pittsford, NY (US); Charles E. Sparks, Pittsford, NY (US); Daniel H. Ryan, Pittsford, NY (US); Arthur J. Moss, Rochester, NY (US)

(73) Assignee: University of Rochester, Rochester, NY (US)

( * ) Notice: Subject to any disclaimer, the term of this patent is extended or adjusted under 35 U.S.C. 154(b) by 1995 days.

(21) Appl. No.: 11/809,832

(22) Filed: May 31, 2007

(65) Prior Publication Data

US 2008/0009684 A1   Jan. 10, 2008

Related U.S. Application Data

(60) Provisional application No. 60/809,460, filed on May 31, 2006, provisional application No. 60/809,760, filed on May 31, 2006, provisional application No. 60/809,481, filed on May 31, 2006.

(51) Int. Cl.
*A61B 5/00*          (2006.01)
*G06F 19/00*         (2011.01)
(Continued)

(52) U.S. Cl.
CPC .......... *A61B 5/7271* (2013.01); *G06F 19/3431* (2013.01); *G06F 19/3487* (2013.01); *A61B 5/7275* (2013.01); *A61B 5/00* (2013.01); *G06F 19/345* (2013.01); *G06T 17/00* (2013.01);
(Continued)

(58) Field of Classification Search
CPC . G06F 19/3431; G06F 19/3487; G06F 19/36; A61B 5/7275; G06Q 50/22; G06Q 50/24; G06T 17/00; G06T 22/2116

USPC ........ 600/300–301, 481–483, 508, 515, 529; 128/898, 897, 920–925; 345/419, 440, 345/428, 581; 705/2–4
See application file for complete search history.

(56) References Cited

U.S. PATENT DOCUMENTS 5,008,752 A * 4/1991 Van Nostrand ............... 348/581
5,903,273 A * 5/1999 Mochizuki et al. ........... 345/423
(Continued)

OTHER PUBLICATIONS

Carr, C. J. et al "Surface Interpolation with Radial Basis functions for medical imaging", IEEE Transactions on Medical Imaging, vol. 16, No. 1, Feb. 1997, p. 96-107.*

(Continued)

*Primary Examiner* — William Thomson
*Assistant Examiner* — Marie Archer
(74) *Attorney, Agent, or Firm* — James W. Hill; McDermott Will & Emery LLP

(57) ABSTRACT

Described is a method of determining the relative risk of an outcome based on an analysis of multiple risk factors. A graphical method is used to take values corresponding to risk parameters and an event outcome to produce a smoothed surface map representing relative risk over an entire space defined by n risk factors. Applying a query data point to the surface map permits the determination of the estimated outcome probability for the query data point, based on its location on the surface map. The method then reports a relative risk or other probability measure associated with the query data point. Also described is a method of analysis in which subpopulations previously identified as high-risk can be further analyzed with respect to risk posed by additional factors.

37 Claims, 15 Drawing Sheets

Surface map of estimated prevalence of recurrent coronary events as a function of cholesterol and CRP ranks in the study population of 767 non-diabetic postinfarction patients.

(51) Int. Cl.
  *G06Q 50/00* (2012.01)
  *G06T 17/00* (2006.01)
  *A61B 5/145* (2006.01)

(52) U.S. Cl.
  CPC ......... *G06T2215/16* (2013.01); *A61B 5/14532* (2013.01); *G01N 2800/04* (2013.01); *G01N 2800/60* (2013.01); *Y10S 707/99937* (2013.01); *Y10S 707/9994* (2013.01); *Y10S 128/92* (2013.01); *Y10S 128/923* (2013.01)
  USPC ............ 600/300; 705/2; 705/3; 707/999.007; 707/999.01; 128/920; 128/923; 345/419; 345/440

(56) References Cited

U.S. PATENT DOCUMENTS

| | | | | |
|---|---|---|---|---|
| 5,953,465 | A * | 9/1999 | Saotome | 382/300 |
| 6,059,724 | A * | 5/2000 | Campell et al. | 600/300 |
| 6,263,120 | B1 * | 7/2001 | Matsuoka | 382/300 |
| 7,483,917 | B2 * | 1/2009 | Sullivan et al. | 1/1 |
| 2002/0128858 | A1 * | 9/2002 | Fuller | 705/1 |
| 2004/0133358 | A1 * | 7/2004 | Bryant et al. | 702/19 |
| 2005/0119534 | A1 * | 6/2005 | Trost et al. | 600/300 |
| 2006/0173663 | A1 * | 8/2006 | Langheier et al. | 703/11 |
| 2007/0015170 | A1 * | 1/2007 | Salonen et al. | 435/6 |
| 2007/0099242 | A1 * | 5/2007 | Heinecke et al. | 435/7.2 |
| 2007/0173700 | A1 * | 7/2007 | Ishihara et al. | 600/300 |

OTHER PUBLICATIONS

Lee, Y-T, et al, Morphology-based three-dimensional interpolation, IEEE Transactions on Medical Imaging, vol. 19, No. 7, Jul. 2000, p. 711-721.*

Sobel, B. E. et al., in "Increased Plasminogen Activator Inhibitor Type 1 in Coronary Artery Atherectomy Specimens From Type 2 Diabetic Compared with nondiabetic patients: A potential factor predisposing to thrombosis and its persistence", Circulation, 1998; 97; 2213-2221.*

Corsetti, J. P. et al. "Serum glucose and triglyceride determine high-risk subgroups in non-diabetic postinfarction patients", Atherosclerosis 183 (2005) 293-300.*

McGregor, E. et al., "Proteomics of heart disease", Human Molecular Genetics, 2003, vol. 12, Review Issue 2, R135-R144.*

* cited by examiner

Surface map of estimated prevalence of recurrent coronary event outcome as a function of cholesterol–lipoprotein (total cholesterol, apoB, apoAI, and HDL) and inflammation (CRP, fibrinogen, d-dimer, and vWF) factor score ranks in the study population of 767 non-diabetic postinfarction patients.

Surface map of estimated prevalence of recurrent coronary events as a function of cholesterol and CRP ranks in the study population of 767 non-diabetic postinfarction patients.

FIG. 3

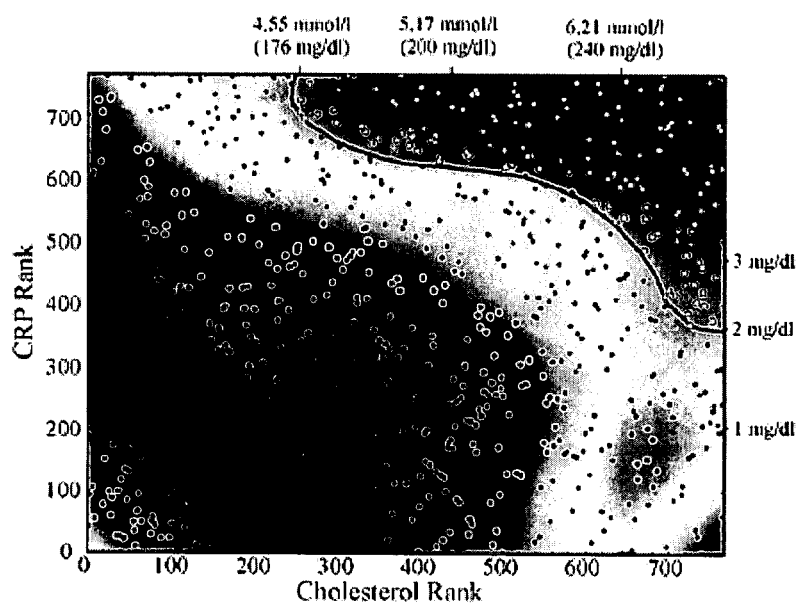

Contour map of estimated prevalence of recurrent coronary events as a function of cholesterol rank and CRP rank in the study population of 767 non-diabetic postinfarction patients. Superimposed is the isoprevalence contour line (red line) at 0.19 that divides high-risk patients (open circles) from low-risk patients (filled circles). Estimated prevalences are: dark green (0.10), light green (0.15), yellow-orange (0.20), and red (0.25).

Kaplan–Meier curves of patients in presumptive high-risk subgroup (lower curve, $N = 149$) vs. lower risk subgroup (upper curve, $N = 618$) (log-rank statistic, $p = 0.024$).

FIG. 5

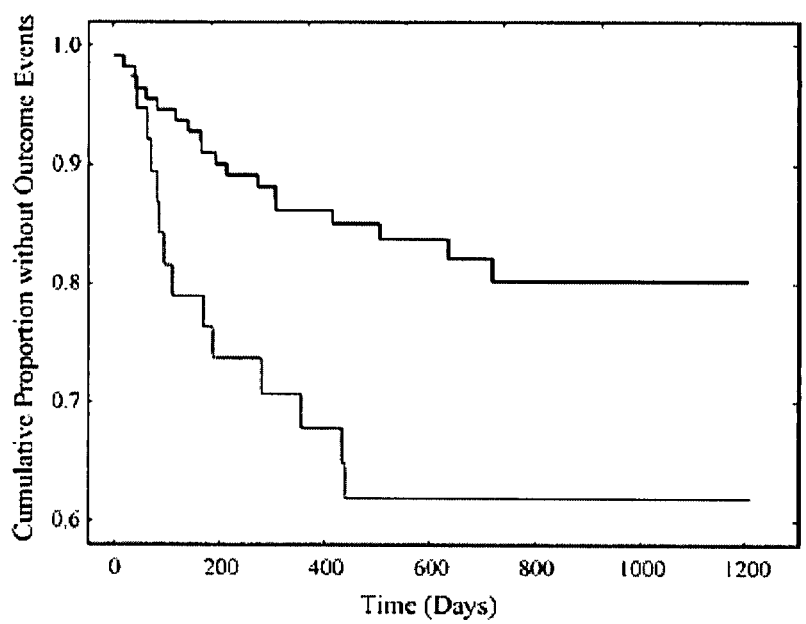

Kaplan–Meier curves of patients in high-risk subgroup ($N = 149$) divided into two groups based on HDL cholesterol concentration with one group having values of HDL levels within the combined three quartiles of lowest HDL ($N = 111$) and the other having values of HDL levels within the highest HDL quartile ($N = 38$). Curves are: lowest three HDL quartiles—upper line and highest HDL quartile—lower line (log-rank statistic, $p = 0.012$).

FIG. 6

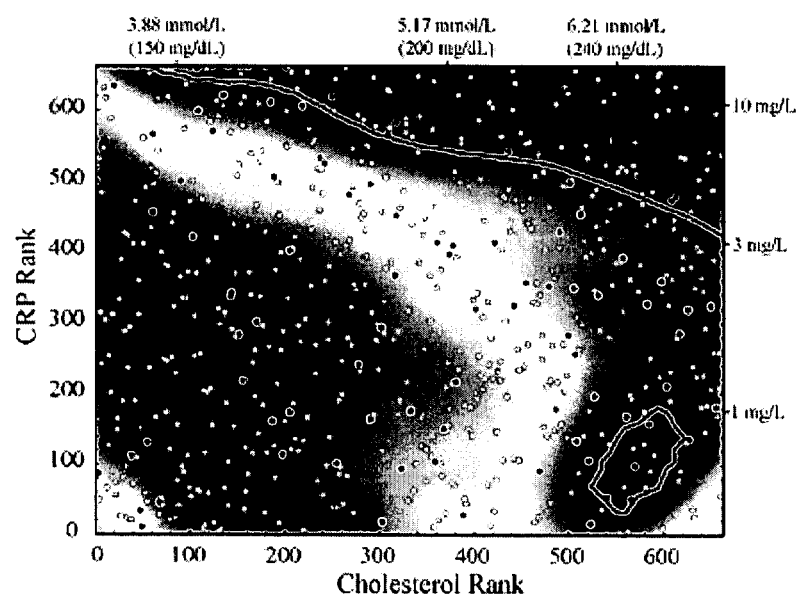

Contour plot of estimated recurrent coronary event rate as a function of cholesterol and CRP ranks (highest rank corresponding to highest concentration level) for study population of postinfarction patients ($N = 663$) with isoprevalence lines at outcome event rate of 0.20 superimposed. Patients with recurrent coronary events, solid circles; patients without recurrent coronary events, open circles. Color scale for estimated outcome event prevalence is: green 0.10, light green 0.14, yellow 0.18, orange 0.20, red 0.23 and dark red 0.28.

FIG. 7

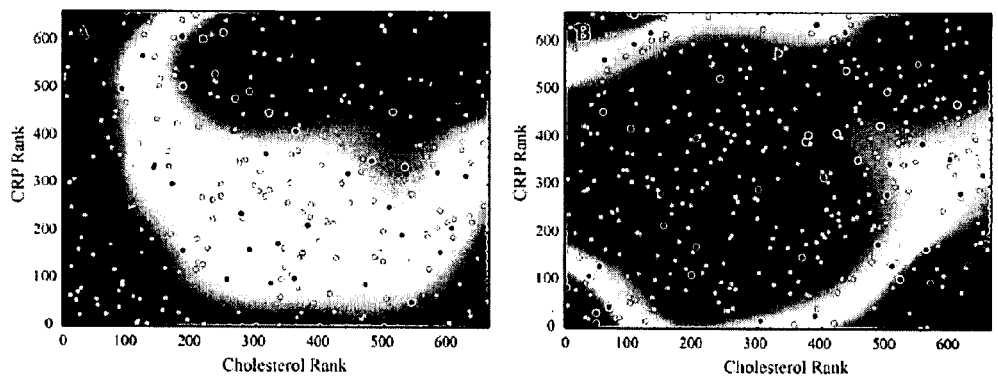

Contour plots of estimated recurrent coronary event rate as a function of cholesterol and CRP ranks (highest rank corresponding to highest concentration level) for study population of postinfarction patients (N = 663) for patients with CC variant (Panel A) and for patients with CT or TT variants (Panel B). Patients with recurrent coronary events, solid circles; patients without recurrent coronary events, open circles. Color scale for estimated outcome event prevalence for the two plots is: green 0.05, light green 0.10, yellow 0.18, orange 0.25, red 0.32 and dark red 0.45. Refer to Fig. 1 for absolute concentrations of cholesterol and CRP.

FIG. 8A

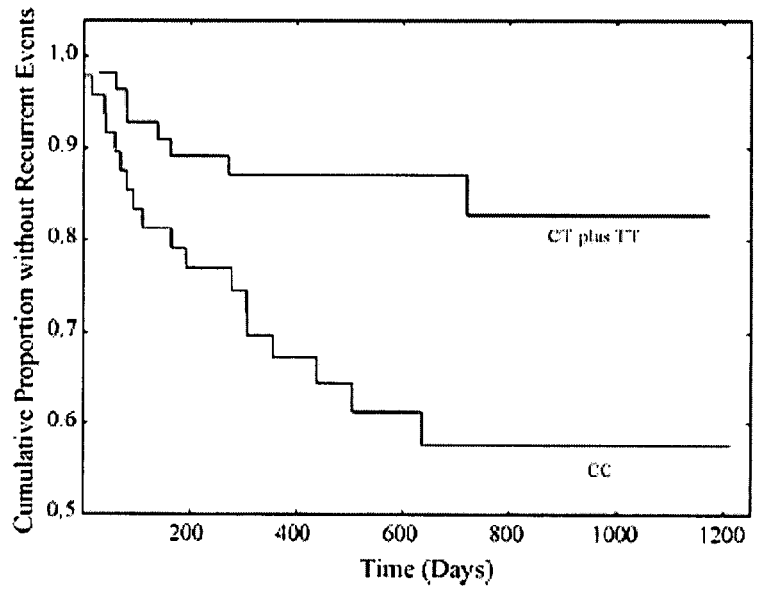

Kaplan–Meier curves of patients in high-risk subgroup showing cumulative proportion of patients without recurrent events as a function of C242T polymorphism of p22phox subunit. CT plus TT variants ($N = 55$), heavy line; CC variant ($N = 48$), light line ($p = 0.0073$).

FIG. 8B

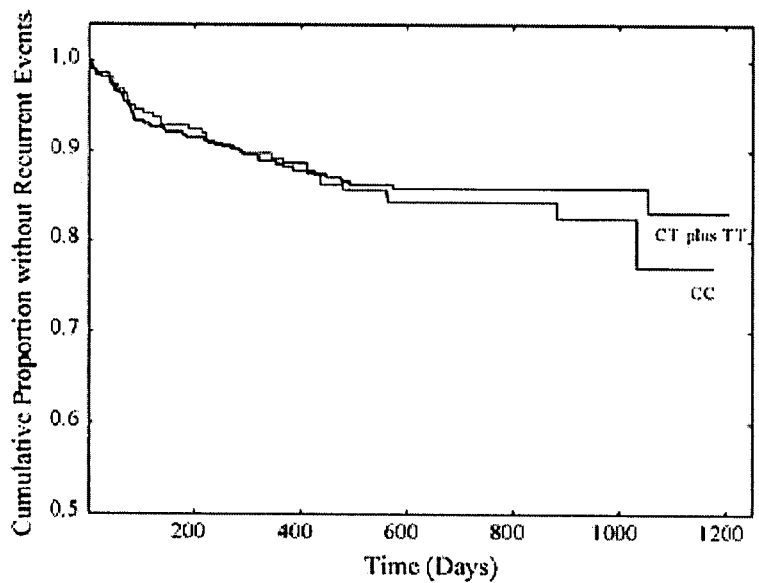

Kaplan–Meier curves of patients in the low-risk subgroup subgroup showing cumulative proportion of patients without recurrent events as a function of C242T polymorphism of p22phox subunit. CT plus TT variants ($N = 332$), heavy line; CC variant ($N = 228$), light line ($p = 0.59$).

FIG. 9

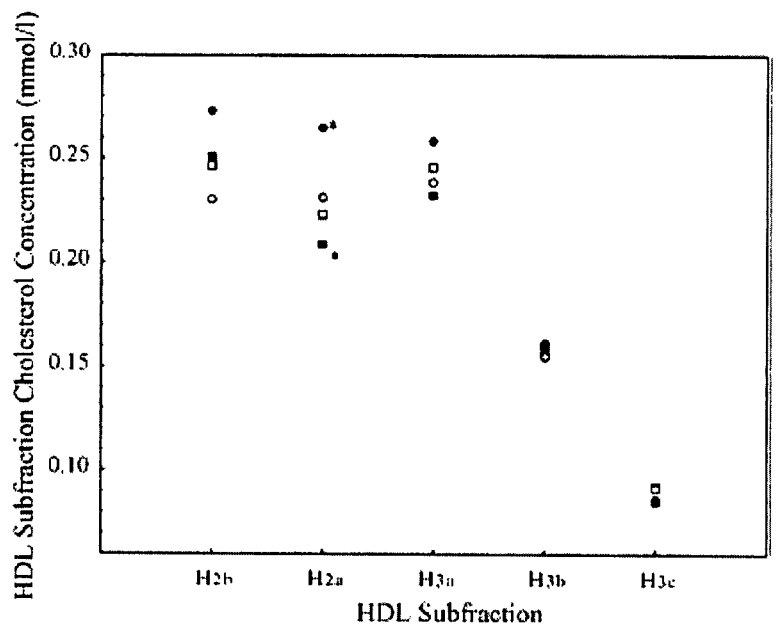

Mean HDL subfraction cholesterol concentrations in the low-risk and high-risk subgroups as a function of absence or presence of recurrent coronary events (approximate range in HDL subfraction size (nms) were as follows: $H_{2b}$, 9.7–12.9; $H_{2a}$, 8.8–9.7; $H_{3a}$, 8.2–8.8; $H_{3b}$, 7.8–8.2; $H_{3c}$, 7.2–7.8). Low-risk subgroup without events, open squares; low-risk subgroup with events, solid squares; high-risk subgroup without events, open circles; high-risk with events, solid circles. Significant differences among individual subfractions (Kruskal-Wallis) existed only for $H_{2a}$ in the high-risk subgroup with events vs. the low-risk subgroup with events ($^*p = 0.003$).

Surface map of estimated prevalence of recurrent coronary events as a function of glucose and triglyceride ranks in the total 767 non-diabetic postinfarction patients. Ranking of independent variables was from lowest to highest concentration values with rank 1 corresponding to the lowest concentration.

FIG. 11

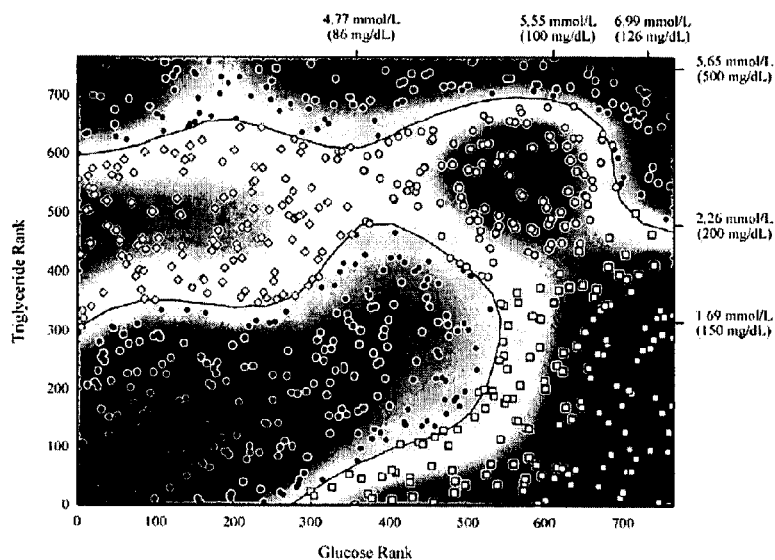

Contour map of estimated prevalence of recurrent coronary events as a function of glucose and triglyceride ranks in the total 767 non-diabetic postinfarction patients with superimposed isoprevalence lines of 0.16. Ranking of independent variables was from lowest to highest concentration values with rank 1 corresponding to the lowest concentration. Patient subgroups are as follows: baseline patients – solid circles, subgroup 1 – diamonds, subgroup 2 – hollow circles, and subgroup 3 – squares. Color scale is estimated prevalence as follows: dark green – 0.08, light green – 0.12, yellow – 0.16, orange – 0.20, and bright red – 0.24.

Kaplan–Meier curves of baseline and high-risk patient subgroups. Curves are: baseline – heavy solid line, subgroup 1 – light solid line, subgroup 2 – dashed line, and subgroup 3 – dotted line. Log rank statistic $p$-values for each of the subgroups vs. baseline were 0.016, 0.001, and 0.024, respectively.

Kaplan-Meier curves of proportion of patients without recurrent coronary events as a function of Gp-1b variant for diabetic patients (log rank $P = 0.013$) and for nondiabetic patients (log rank $P = 0.49$) as labeled.

FIG. 14

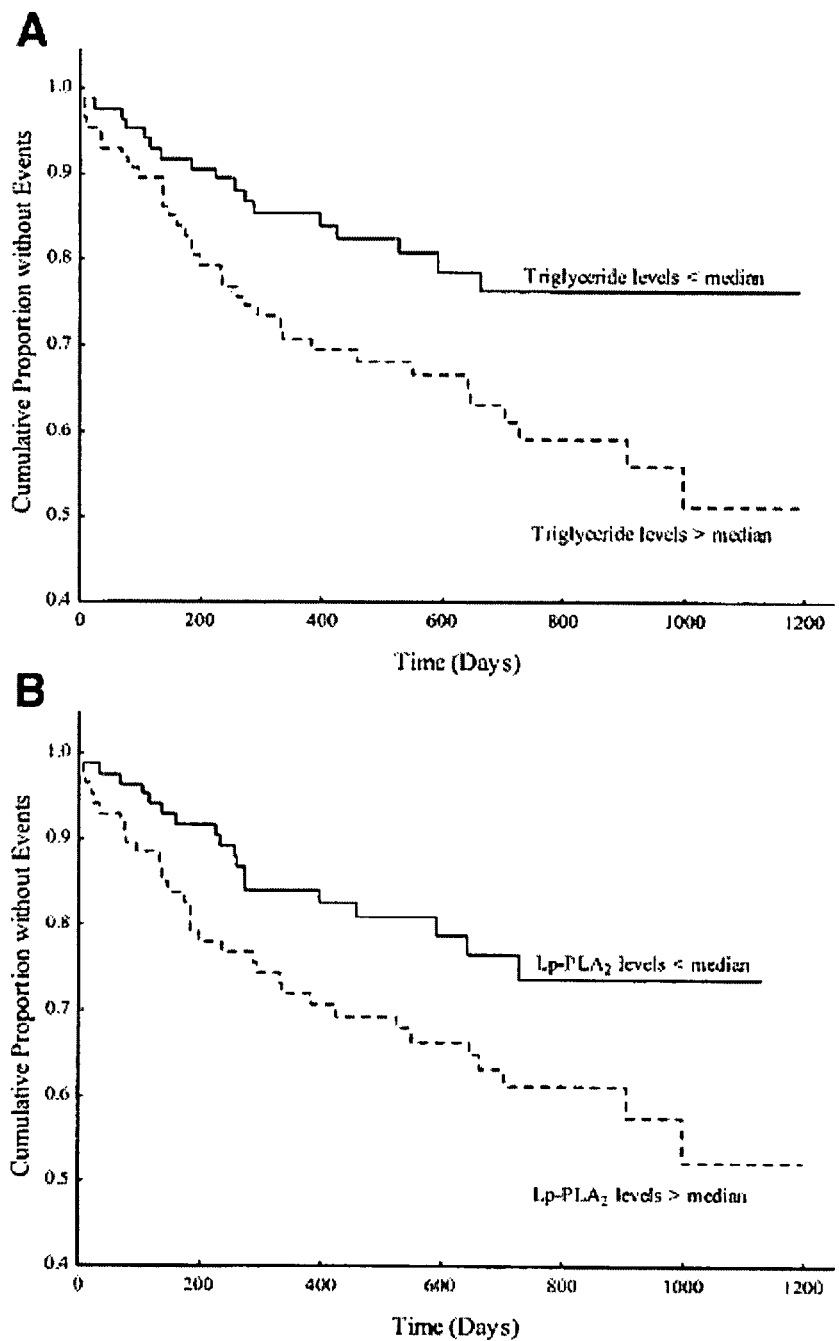

Kaplan-Meier curves of diabetic patients showing proportion without recurrent coronary events. A: Curves as a function of triglycerides dichotomized according to the 50th percentile (log rank $P = 0.015$). B: Curves as a function of Lp-PLA$_2$ dichotomized according to the 50th percentile (log rank $P = 0.031$). Solid line, <50th percentile in concentration; dashed line, >50th percentile in concentration.

FIG. 15

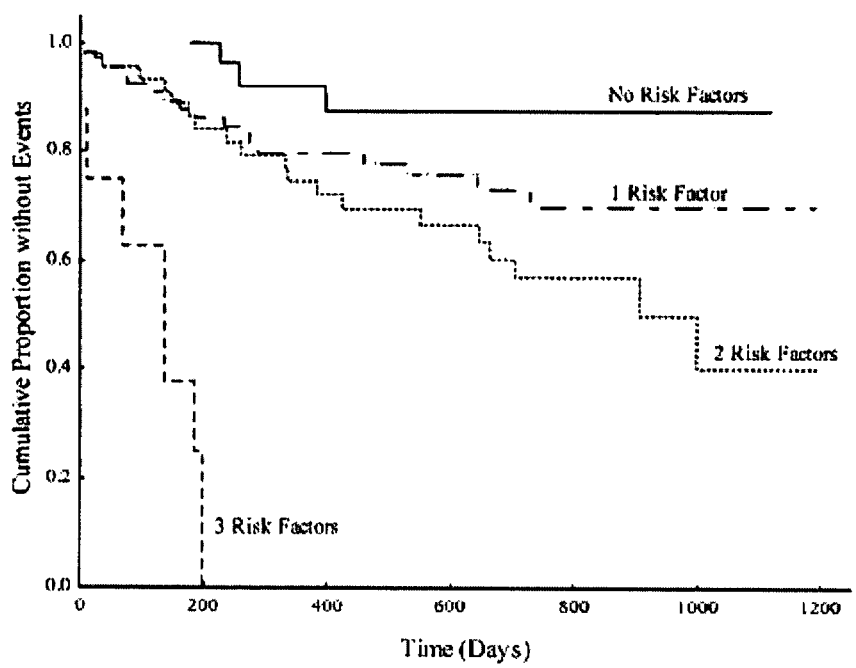

Kaplan-Meier curves of diabetic patients showing proportion without recurrent coronary events as a function of number of risk factors (Gp-1b variant, triglyceride, and Lp-PLA$_2$). Log rank $P$ values for comparison of curves relative to patients with no risk factors are as follows: one risk factor, $P = 0.15$; two risk factors, $P = 0.018$; and three risk factors, $P < 0.00001$. Solid line, patients with no risk factors; line with long and short dashes, patients with one risk factor; dotted line, patients with two risk factors; line with short dashes, patients with three risk factors.

IDENTIFYING RISK OF A MEDICAL EVENT

RELATED APPLICATIONS

This application claims the benefit under 35 U.S.C. §119 (e) of U.S. Provisional Application 60/809,460, filed May 31, 2006, and entitled "Methods and Systems of Identifying an Increased Risk of a Coronary Event Based on Elevated HDL Levels"; U.S. Provisional Application No. 60/809,760, filed May 31, 2006, and entitled "Methods and Systems of Identifying an Increased Risk of a Coronary Event Based on Elevated HDL Levels"; and U.S. Provisional Application No. 60/809,481, filed May 31, 2006, and entitled "Methods and Systems of Identifying an Increased Risk of a Coronary Event Based on Serum Glucose and Triglyceride Levels"; the entire contents of all of these applications being hereby incorporated by reference herein.

GOVERNMENT LICENSE RIGHTS

The U.S. Government has a paid-up license in this invention and the right in limited circumstances to require the patent owner to license others on reasonable terms as provided for by the terms of Grant No. HL-48259, awarded by the National Institutes of Health.

FIELD OF THE INVENTION

The invention is related to systems and methods of identifying patients having increased risk of an adverse medical outcome, such as a coronary event.

BACKGROUND OF THE INVENTION

The recognition of factors that define patient subgroups having increased risk for the occurrence of various diseases or medical outcomes, as well as the identification of individuals who potentially belong to such subgroups, is becoming increasingly important in diagnostic medicine. This is especially true as patient management involves individualized approaches that consider genetic and environmental risk factors on a case by case basis.

Cardiovascular disease is a leading cause of death in developed countries. Because of its prevalence, identifying certain risk factors which increase the incidence of cardiovascular disease are considered to be especially useful in terms of designing therapies and other approaches to reducing the incidence of coronary events, or for improving outcomes after such an event has occurred. For example, it has long been known that the development of atherosclerotic plaque, if left untended, will typically lead to myocardial infarction (MI). It is also becoming increasingly clear that inflammation is a significant factor in development of atherosclerosis.

Two recent studies report beneficial effects on cardiovascular disease (CVD) risk of statin-induced reductions in C-reactive protein (CRP) levels that were independent of concomitant reductions in levels of atherogenic lipoproteins (Ridker et al., N. Engl. J. Med. 352: 20-28, 2005; Nissen et al., N. Engl. J. Med. 352: 29-38, 2005). These studies are part of an evolving literature demonstrating importance of inflammatory processes in atherogenesis, an area where lipoprotein-associated CVD risk has already been well established.

SUMMARY OF THE INVENTION

As the nature of interactions, for example that of inflammation responses with traditional lipoprotein risk factors, is largely unknown, considerable attention should be focused on studies of such interactions in connection with, for example, development of CVD risk. In view of the potentially important role of interactions of inflammation with lipoproteins in the development of atherosclerosis, there is a need to identify patient subgroups at high risk for recurrent coronary events simultaneously dependent on measures of inflammation and atherogenic lipoproteins together. Further, it would be desirable based on a knowledge of various relevant risk factors to be able to assign individual patients to risk subgroups based on predictive value of risk factors analysis in order to better provide individualized patient management with respect to reducing or obviating the risk of MI.

Accordingly, in some embodiments there is provided a method for identifying risk of a medical outcome based on an analysis of multiple risk factors, comprising: providing a reference database comprising a plurality of reference data points, each reference data point comprising a value for each of n risk-factor parameters, wherein n≥2; wherein each reference data point further comprises a corresponding outcome value; and wherein the outcome value is determined by the prior occurrence or non-occurrence of a medical outcome; mapping each reference data point as a map point in (n+1)-dimensional space, thereby producing a reference map; wherein the position of each map point in n dimensions is determined by the values of the associated reference point's n risk-factor parameters; and wherein the position of each map point in the (n+1)th dimension is determined by the outcome value for the associated reference data point; applying an interpolation algorithm to the reference map to produce an interpolated (n+1)-dimensional map; wherein the interpolated (n+1)-dimensional map comprises a surface that defines a function that maps values for the n risk-factor parameters to predicted outcome values; and wherein each of the predicted outcome values represents a relative risk and a probability of occurrence of the medical outcome; mapping a query data point, comprising values for each of the n risk-factor parameters, onto the interpolated (n+1)-dimensional map; wherein the location of the query data point on the interpolated (n+1)-dimensional map is determined, at least in part, by the query data point's values of the n risk-factor parameters; determining a predicted outcome value for the query data point by mapping, with the function, the query data point's values of the n risk-factor parameters to a point in the surface, the point in the surface being indicative of the predicted outcome value for the query data point; outputting at least one of the query data point's predicted outcome value and its associated relative risk to an output device.

In some embodiments, n=2.

In some embodiments, the outcome comprises a coronary event in a patient. In some embodiments the coronary event comprises at least one of a malignant arrhythmia, a myocardial infarction, and an episode of unstable angina.

In some embodiments, the relative risk value comprises an increased risk value.

In some embodiments, at least one of the risk-factor parameters comprises a continuous range of values. In some embodiments, at least one of the risk-factor parameters comprises a range of discrete values. In some embodiments, the discrete value comprises a binary range of values. In some embodiments, at least one of the risk-factor parameters comprises a presence or absence of a risk factor, a pre-existing condition, or a history of a pre-existing condition.

In some embodiments, the relative risk represented by the query data point's predicted outcome value comprises a range of values of relative risk.

In some embodiments, the surface comprises points representing values or functions of probabilities of occurrence of the medical outcome.

In some embodiments, the method further comprises outputting a graphical representation of the interpolated (n+1)-dimensional map to an output device.

In some embodiments, the output device comprises at least one of a numerical display, a graphical display, an electronic monitor, paper, an LCD, and a hand-held display.

In some embodiments, at least one of the n risk-factor parameters is selected from the group consisting of blood levels of apoA1, apoB, total serum cholesterol, HDL, cholesterol, triglyceride, glucose, insulin, plasminogen activator inhibitor-1, lipoprotein (a), C-reactive protein, von Willibrand factor antigen, fibrinogen, D-dimer, Factor VII, Factor VIIa, and lipoprotein-associated phospholipase $A_2$.

In some embodiments, at least one of the n risk-factor parameters is selected from the group consisting of an LDL peak particle diameter, a history of type II diabetes, a history of a pre-diabetic syndrome, a history of metabolic syndrome, a polymorphism in NAD(P)H oxidase, a polymorphism in Glycoprotein-Ibα, a history of obesity, a body mass index, and a history of a previous coronary event.

In some embodiments, the coronary event comprises at least one of a malignant arrhythmia, a myocardial infarction, and an episode of unstable angina.

In some embodiments, two of the risk-factor parameters comprise a genetic polymorphism in NAD(P)H oxidase and a serum HDL level.

In some embodiments, an additional risk-factor parameter comprises a C-reactive protein level and a cholesterol level.

In some embodiments, the polymorphism comprises a polymorphism in the p22phox subunit of the NAD(P)H oxidase.

In some embodiments, the polymorphism comprises a C or T nucleotide at position +242 of the NAD(P)H oxidase gene p22phox subunit.

In some embodiments, the polymorphism further comprises a homozygosity for a C nucleotide at position +242 of the NAD(P)H oxidase gene p22phox subunit.

In some embodiments, the HDL is $H_{2a}$ HDL.

In some embodiments, the HDL is an HDL sub-fraction comprising particles corresponding in size to $H_{2a}$ HDL particles.

In some embodiments, two of the risk-factor parameters comprise two of the following: a serum HDL level, a CRP level, and a total serum cholesterol level.

In some embodiments, one of the risk-factor parameters comprises a history of a prior myocardial infarction.

In some embodiments, two of the risk-factor parameters comprise a body fluid glucose level and a serum triglyceride level. In some embodiments the body fluid comprises at least one of serum and cerebrospinal fluid.

In some embodiments, total serum cholesterol level is at least about 4.5 mmol/L, at least about 5.0 mmol/L, at least about 5.5 mmol/L, or at least 6.0 mmol/L.

In some embodiments, serum CRP level is at least about 2.0 mg/dL, at least about 2.2 mg/dL, at least about 2.5 mg/dL, at least about 2.8 mg/dL, at least about 3.0 mg/dL, or at least about 3.3 mg/dL.

In some embodiments, serum HDL level is at least about 1.00 mmol/L, at least about 1.05 mmol/L, at least about 1.10 mmol/L, at least about 1.12 mmol/L, or at least about 1.15 mmol/L.

In some embodiments, serum HDL comprises HDL particles having a median particle size of at least about 8.8 nm, at least about 8.85 nm, at least about 8.9 nm, or at least about 9.0 nm.

In some embodiments, a risk factor parameter comprises an apoA1 level of at least about 1.25 g/L, at least about 1.3 g/L, at least about 1.35 g/L, at least about 1.4 g/L, at least about 1.45 g/L, or at least about 1.55 g/L. In some embodiments, a risk factor parameter comprises an apoA1 level in a range from about 1.25 g/L to about 1.70 g/L.

In some embodiments, two of the risk-factor parameters comprise a body mass index and a fibrinogen level.

In some embodiments, one of the risk-factor parameters comprises a plasminogen activator inhibitor level. In some embodiments, the plasminogen activator inhibitor is plasminogen activator inhibitor-1 (PAI-1).

In some embodiments, serum glucose levels are less than about 4.8 mmol/L, less than about 4.6 mmol/L, or less than about 4.3 mmol/L.

In some embodiments, serum triglyceride levels are greater than about 1.6 mmol/L, greater than about 1.7 mmol/L, greater than about 2.1 mmol/L, or greater than about 2.3 mmol/L.

In some embodiments, a risk factor parameter further comprises a prior myocardial infarction.

In some embodiments, a risk-factor parameter comprises a history of metabolic syndrome.

In some embodiments, PAI-1 levels are greater than about 40 μg/L, greater than about 45 g/L, or greater than about 47 μg/L.

In some embodiments, the genetic polymorphism in Glycoprotein-Ibα comprises a threonine or a methionine residue at amino acid residue 145 of Glycoprotein-Ibα. In some embodiments, the polymorphism comprises having at least one Glycoprotein-Ibα that encodes Met at amino acid residue 145.

In some embodiments, one of the risk-factor parameters comprises a history of diabetes.

In some embodiments, one of the risk-factor parameters comprises a triglyceride level. In some embodiments, one of the risk-factor parameters comprises a lipoprotein-associated phospholipase $A_2$ level.

In some embodiments there is provided a method of identifying or estimating risk of a medical outcome in a population and a subpopulation of patients, comprising: providing a first plurality of reference data points representing a population of patients, each reference data point comprising a value for each of n risk-factor parameters, wherein n≥2; wherein each reference data point further comprises a corresponding outcome value; and wherein the outcome value is determined by the prior occurrence or non-occurrence of a medical outcome; mapping each reference data point as a map point in (n+1)-dimensional space, thereby producing a reference map; wherein the position of each map point in n dimensions is determined by the values of the associated reference point's n risk-factor parameters; and wherein the position of each map point in the (n+1)th dimension is determined by the outcome value for the associated reference data point; applying an interpolation algorithm to the reference map to produce an interpolated (n+1)-dimensional map; wherein the interpolated (n+1)-dimensional map comprises a surface that defines a function that maps values for the n risk-factor parameters to predicted outcome values; and wherein each of the predicted outcome values represents at least one of a relative risk and a probability of occurrence of the medical outcome; locating on the interpolated (n+1)-dimensional map a first subpopulation of reference date points corresponding to a first subpopulation of patients within the population of patients, the first subpopulation of reference date points representing an increased or decreased risk of the medical outcome relative to other subpopulations of patients within the population; providing a plurality of subpopulation data points corresponding to the first subpopulation of patients, each subpopulation data point comprising a value for each of m risk-factor parameters, wherein m≥2; wherein each subpopulation data point further comprises a corresponding outcome value; and wherein the outcome value is determined by the prior occurrence or non-occurrence of the medical outcome; mapping each subpopulation data point as a map point in (m+1)-dimensional space, thereby producing a second reference map; wherein the position of each map point in m dimensions is determined by the values of the associated subpopulation data point's m risk-factor parameters; and wherein the position of each map point in the (m+1)th dimension is determined by the outcome value for the associated subpopulation data point; applying an interpolation algorithm to the second reference map to produce an interpolated (m+1)-dimensional map; wherein the interpolated (m+1)-dimensional map comprises a second surface that defines a second function that maps values for the m risk-factor parameters to subpopulation predicted outcome values; and wherein each of the subpopulation predicted outcome values represents at least one of a subpopulation relative risk and a subpopulation probability of occurrence of the medical outcome.

BRIEF DESCRIPTION OF THE DRAWINGS

FIG. 3 is a contour map of estimated prevalence of recurrent coronary events as a function of cholesterol rank and CRP rank in non-diabetic post-infarction patients, with a superimposed isoprevalence line of 0.19.

FIG. 5 is a graph of Kaplan-Meier curves of patients in high-risk subgroup divided into two groups based on HDL cholesterol concentration with one group having values of HDL levels within the combined three quartiles of lowest HDL, and the other having values of HDL levels within the highest HDL quartile.

FIG. 6 is a contour plot of estimated recurrent coronary event rate as a function of cholesterol rank and CRP rank in a population of post-infarction patients with isoprevalence lines at an outcome rate of 0.20 superimposed.

FIG. 7 is two contour plots of estimated recurrent coronary event as a function of cholesterol and CRP ranks for patients with the CC p22phox variant (panel A) and patients with the CT or TT p22phox variant (panel B).

FIG. 8A is a graph of Kaplan-Meier curves of patients in a high-risk subgroup, showing cumulative proportion of patients without recurrent events as a function of the C242T polymorphism of the p22phox subunit.

FIG. 8B is a graph of Kaplan-Meier curves of patients in a low-risk subgroup, showing cumulative proportion of patients without recurrent events as a function of C242T polymorphism in the p22phox subunit.

FIG. 9 is a graph of HDL subfraction cholesterol concentrations in baseline and high-risk subgroups as a function of absence or presence of recurrent coronary events.

FIG. 11 is a contour map of estimated prevalence of recurrent coronary events as a function of glucose and triglyceride in non-diabetic post-infarction patients, with superimposed isoprevalence lines of 0.16.

FIG. 14; panel A is a Kaplan-Meier curve of diabetic patients showing the proportion without recurrent coronary events. The curve is provided as a function of triglycerides dichotomized according to fiftieth percentile (log rank p, 0.015). Solid lines represent less than 50th percentile in concentration; dashed lines represent greater than 50th percentile in concentration.

FIG. 14; panel B provides a Kaplan-Meier curve as a function of Lp-$PLA_2$ dichotomized according to fiftieth percentile (log rank p, 0.031). Solid lines represent less than 50th percentile in concentration; dashed lines represent greater than 50th percentile in concentration.

FIG. 15 provides Kaplan-Meier curves of diabetic patients without recurrent coronary events as a function of a number of risk factors (Gp-Ibα variant, triglyceride, and Lp-$PLA_2$)

DETAILED DESCRIPTION OF THE INVENTION

Figure 1:
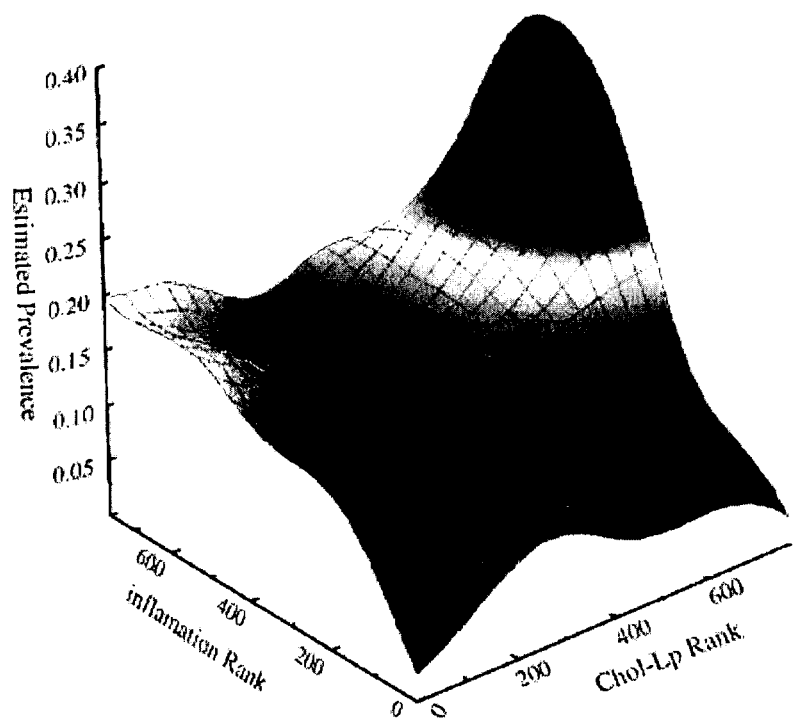
FIG. 1 is a surface map of estimated prevalence of recurrent coronary event outcome as a function of cholesterol-lipoprotein and inflammation in non-diabetic post-infarction patients.

Described herein are novel methods and systems of identifying increased risk of a coronary event in a patient. In some embodiments, the method involves identifying one or more variables and correlating the variables with an increase likelihood of a coronary event in a patient. Unless otherwise indicated, the term "coronary event" is a broad term and is used in its ordinary sense and includes, without limitation, and wherein the context permits, unstable angina, cardiac death, MI, congestive heart failure, ventricular arrhythmias, atrial arrhythmias, and angiographic total coronary occlusion.

In some embodiments, the patient is a human without any previous incidence of a coronary event. In some embodiments, the patient is a human with a previous incidence of a coronary event. In some embodiments, the patient is a human with a previous incident of a myocardial infarction. In some embodiments, the patient may be an obese patient. In some embodiments, the patient may be diabetic. In some embodiments, the patient is a non-diabetic. In some embodiments, the patient has metabolic syndrome as further described herein. In some embodiments the patient may present one or more physiological conditions that can be associated with increased risk of cardiovascular disease. In some embodiments, the patient may present none of the traditionally recognized risk factors associated with increased risk of cardiovascular disease.

Methods of identifying an increased risk of a coronary event in a patient or group of patients can comprise identifying certain high risk factors that correlate to an increased risk of a coronary event. In some cases, the combination of different risk factors may be predictive of an increase (or in some cases decrease) in the likelihood of a coronary event.

Some variables, which in some cases are risk factors, include, without limitation, levels of apolipoprotein-B (apoB), total cholesterol (Chol), apolipoprotein-A1 (apoA1), high density lipoprotein cholesterol (HDL), and triglyceride (Trig), LDL peak particle diameter (PPD), levels of glucose (Glu), insulin (Ins), body mass index (BMI), plasminogen activator inhibitor-1 (PAI-1), lipoprotein(a) (Lp(a)), C-reactive protein (CRP), von Willebrand factor antigen (vWF), fibrinogen (Fibr), D-dimer (D-dim), Factor VII (FVII), and Factor VIIa (FVIIa).

In some embodiments, variables related to an increased likelihood of a coronary event in a patient are also risk factors associated with the development of atherosclerosis. These include, but are not limited to, inflammation, cholesterol levels, and lipoprotein levels and characteristics. Inflammation can be indicated by the levels of one or more of CRP, fibrinogen, D-dimer, or vWF. Measurements of cholesterol and measurements of lipoproteins may include, but are not limited to, one or more levels of total cholesterol, apoAI, apoB, HDL, LDL, and Lp(a).

In some embodiments, risk factors that increase the likelihood of a coronary event in some patients are those generally associated with multiple sclerosis (MS). These can include, but are not limited to, atherogenic dyslipidemia, hypertension, and elevated blood glucose. Atherogenic dyslipidemia consists of an aggregation of lipoprotein abnormalities including elevated serum triglyceride and apoB, increased small LDL particles, and a reduced level of HDL cholesterol. Risk factors associated with MS may also include, abdominal obesity, insulin resistance, physical inactivity, aging, and hormonal imbalance. Thus, many risk factors may contribute to the development of metabolic syndrome and directly promote the development of atherosclerotic disease. In diagnosing the increased risk of a coronary event, some specific factors play more significant roles than other risk factors. Furthermore, there may be as yet unidentified risk factors that either alone, or in combination with other factors, result in significantly increased risk of a person suffering a coronary event.

Therefore, specific risk factors which may increase the risk of a coronary event are sought. In some patients, an increase in the risk of a coronary event is associated with aspects of glycemia and dyslipidemia. Risk factors generally associated with these conditions include elevated serum glucose and elevated serum triglyceride levels. In some embodiments, risk factors comprise fasting serum glucose and triglyceride levels. In other embodiments, risk factors comprise postprandial serum glucose and triglyceride levels.

Three-Dimensional Mapping to Identify Risk Subgroups Within Populations

To this end, we have sought to identify such patient subgroups as related to cardiovascular disease risk in non-diabetic postinfarction patients based upon a set of blood markers as predictors of risk. Significantly, our approach involves a graphical screening procedure that acknowledges that high-risk subgroups could occur anywhere within a risk factor domain. This is in contrast to many traditional approaches where risk is presumed only at extremes. Our approach involves generation of three-dimensional outcome prevalence maps from which potentially high-risk subgroups can be identified over a bivariate domain of blood variables. High risk in these subgroups is confirmed by subsequent rigorous statistical testing.

In some embodiments, a method of identifying an increased risk of a coronary event in a patient comprises determining that the patient has a normal serum glucose level, determining that the patient has an elevated serum triglyceride level, correlating the levels of glucose and elevated triglycerides to determine that the patient has the increased risk of the coronary event, and outputting information indicative of the increased risk to an output device.

Unless otherwise indicated, the term "output device" as used herein is a broad term and is used in its ordinary sense and includes, without limitation, wherein the context permits, a voice, paper, a tangible medium of expression, a computer screen, a board, a display. Similarly, "outputting" is a broad term and is used in it ordinary sense and includes, without limitation, speaking, typing, writing, displaying, transmitting, and producing.

In some embodiments, data inputs are received by a processing module. Unless otherwise indicated, the term "processing module" is a broad term and is used in its ordinary sense and includes, without limitation, wherein the context permits, one or more steps, one or more groups, one or more programs, one or more instructions, and one or more processors. It may also refer to logic embodied in hardware or firmware, or to a collection of software instructions, possibly having entry and exit points, written in a programming language, such as, for example, C or C++.

A processing module may be compiled and linked into an executable program, installed in a dynamic link library, or may be written in an interpreted programming language such as, for example, BASIC, Perl, or Python. It will be appreciated that processing modules may be callable from other modules (such as an input module) or from themselves, and/or may be invoked in response to detected events or interrupts. It will be further appreciated that processing modules may be comprised of connected logic units, such as gates and flip-flops, and/or may be comprised of programmable units, such as programmable gate arrays or processors.

Risk Factors

As measures of inflammation and atherogenic lipoproteins, we used inflammatory factor and the cholesterol-lipoprotein factors derived in our previous factor analysis studies (see Corsetti et al., Atherosclerosis, 171: 351-358, 2003; Corsetti et al., Atherosclerosis 177: 367-373, 2004; the entireties of both of which are incorporated herein by reference), and extended the approach in a clinically more meaningful way by using CRP and total cholesterol as best representatives of these factors. Thus, CRP and total cholesterol were used together with an exploratory three-dimensional graphical screening procedure to analyze non-diabetic postinfarction patients of the THROMBO study (Corsetti et al., Atherosclerosis 183:293-300, 2005; the contents of which are incorporated by reference herein) to produce maps of prevalence of recurrent coronary events over the entire terrain defined by CRP and total cholesterol. Details of the THROMBO study have been reported previously (Moss et al., Circulation 99: 2517-22, 1999; the contents of which are incorporated by reference herein). From this complete terrain high-risk subgroups could subsequently be identified.

Recently, vWF was found to be increased in diabetic patients of the THROMBO study, suggesting endothelial damage as a potential risk for recurrent coronary events. In the present disclosure, and as will be discussed below, this was tested by following a genetic variant of the vWF platelet binding site as a marker and correlating the presence of a particular variant with a clinical outcome.

Thus, in some embodiments of the above described method, the serum total cholesterol level is at least about 4.5 mmol/L. In some embodiments, the serum total cholesterol level is at least about 4.8 mmol/L. In some embodiments, the serum total cholesterol level is at least about 5.1 mmol/L. In some embodiments, the serum total cholesterol level is at least about 5.3 mmol/L. In some embodiments, the serum total cholesterol level is at least about 6 mmol/L.

In some embodiments of the above described method, the serum CRP level is at least about 2 mg/dL. In some embodiments, the serum CRP level is at least about 2.2 mg/dL. In some embodiments, the serum CRP level is at least about 2.5 mg/dL. In some embodiments, the serum CRP level is at least about 2.8 mg/dL. In some embodiments, the serum CRP level is at least about 3 mg/dL. In some embodiments, the serum CRP level is at least about 3.3 mg/dL.

As described herein in accordance with some embodiments, an elevated HDL level may pose a risk factor to patients. In some embodiments, an elevated serum HDL level is at least about 1 mmol/L. In some embodiments, an elevated serum HDL level is at least about 1.05 mmol/L. In some embodiments, the elevated serum HDL level is at least about 1.1 μmol/L. In some embodiments, the elevated serum HDL level is at least about 1.12 mmol/L. In some embodiments, the elevated serum HDL level is at least about 1.14 mmol/L.

In some embodiments, the elevated serum HDL may comprise HDL particles of various sizes. In some embodiments, there may be a correlation between the size of the HDL particle and an increased risk of a coronary event in some patients. In some embodiments, the elevated serum HDL comprises HDL particles having an average size of at least about 8.80 nm. In some embodiments, elevated serum HDL comprises HDL particles having an average size of at least about 8.85 nm. In some embodiments, the elevated serum HDL comprises HDL particles having an average size of at least about 8.90 nm. In some embodiments, the elevated serum HDL comprises HDL particles having an average size of at least about 8.95 nm. In some embodiments, the elevated serum HDL comprises HDL particles having an average size of at least about 9.00 nm.

Some embodiments may additionally comprise determining the presence of a certain type of HDL in a patient. In some embodiments, one type of HDL that corresponds to an increased risk of a coronary event is an $H_{2a}$ HDL particle. Another type that may increase the risk of a coronary event is an HDL similar to an $H_{2a}$ HDL particle. In some embodiments, the HDL particles are similar in median particle size to $H_{2a}$ HDL. In some embodiments, the presence of large HDL particles is associated with an increased risk of a coronary event in a patient.

One method for identifying an increased risk of a coronary event in a patient comprises receiving inputs to a processing module, the inputs comprising data indicative of an elevated serum HDL level in the patient, data indicative of a serum CRP level in the patient, and data indicative of a serum total cholesterol level. This method further comprises correlating the inputs in the processing module to determine that the patient has the increased risk of the coronary event and outputting information indicative of the increased risk to an output device.

In some embodiments, a method for identifying an increased risk of a coronary event in a patient having an elevated serum HDL level comprises receiving inputs to a processing module, the inputs comprising data indicative of one or more additional risk factors. In some embodiments, the data may be indicative of a certain a median particle size of HDL particles. In some embodiments, the data may be indicative of an elevated serum apoA1 level. In some embodiments, the data may be indicative of both a median particle size of serum HDL particles and an elevated serum HDL level. This method further comprises correlating the inputs in the processing module to determine that the patient has the increased risk of the coronary event and outputting information indicative of the increased risk to an output device One method for identifying an increased risk of a coronary event in a patient having an elevated serum HDL level comprises receiving inputs to a processing module, the inputs comprising data indicating the patient has a NAD(P)H oxidase polymorphism. This method further comprises correlating the inputs in the processing module to determine that the patient has the increased risk of the coronary event and outputting information indicative of the increased risk to an output device. This method may further comprise receiving inputs of other risk factors which increase the risk of a coronary event in the patient. These additional risk factors may include, but are not limited to, the size and type of HDL particles as described herein.

In some embodiments, a method for identifying an increased risk of a coronary event in a patient having an elevated serum HDL level comprises receiving inputs to a processing module, the inputs comprising data indicative of one or more additional risk factors. In some embodiments the data may be indicative of a certain median particle size of HDL particles. In some embodiments the particle size may correspond to $H_{2a}$ HDL particles. The method may further comprise correlating the inputs in the processing module to determine that the patient has the increased risk of the coronary event and outputting information indicative of the increased risk to an output device.

In some embodiments, a system for identifying an increased risk of a coronary event in a patient comprises an input module and a processing module. In some embodiments, the input module receives inputs, the inputs comprising data indicative of an elevated serum HDL level, data indicative of a serum CRP level, and data indicative of a serum total cholesterol level. The processing module can correlate the one or more levels of an elevated HDL, serum CRP, and serum total cholesterol to determine that the patient has the increased risk of the coronary event. Certain embodiments can also include an output module that outputs information indicative of an increased risk of a coronary event.

Additional embodiments of such systems may have input modules which receive data indicative of one or more a particle size of HDL and a level of apoA1. In these embodiments, the processing module may correlate the one or more of indications of HDL particle size with that of elevated apoA1 levels. Certain embodiments may include an output module that outputs information indicative of an increased risk of a coronary event.

In some embodiments, the system for identifying an increased risk of a coronary event in a patient, comprises an input module and a processing module, the input module receiving inputs indicative of an elevated serum HDL level and/or the presence of a polymorphism of NAD(P)H oxidase. The processing module can correlate the one or more levels of an elevated HDL and the polymorphism to determine that the patient has the increased risk of the coronary event. Certain embodiments may also include an output module that outputs information indicative of an increased risk of a coronary event.

Certain embodiments of such systems can have input modules which receive data indicative of an HDL particle size or type. In some embodiments, the data is indicative of the HDL mean particle size. In some embodiments, data may be indicative of the presence of $H_{2a}$ HDL. In some embodiments, data may be indicative of the presence of an HDL type similar to $H_{2a}$.

Inputs can also comprise data indicating the presence of a polymorphism of NAD(P)H oxidase. In some embodiments, the polymorphism is of the p22phox subunit of the NAD(P)H, herein termed "the C242T polymorphism." The polymorphism is defined with respect to codon 242 of the p22phox amino-acid coding sequence. In the normal variant, codon 242 specifies Thr, (T allele) while in a variant, a Cys residue (C allele) is specified by the codon. A patient who is homozygous for the C allele (a CC patient) has an increased risk of a future coronary event as compared with those who are heterozygous for the polymorphism (CT) or who are homozygous for the T allele (TT patients). Thus, in some embodiments of the method, the inputs will further comprise data indicative of the genotype of the patient as being either CC, CT or TT with respect to the C242T polymorphism site of p22phox.

In any of the described embodiments, an elevated serum CRP level and an elevated serum total cholesterol may be used to determine the increased risk of the coronary event. Thus, data indicative of such levels may be correlated with increased risk of the coronary event, and a result may be outputted accordingly.

In some embodiments, a method, of identifying an increased risk of a coronary event in a patient having an elevated serum HDL level, comprises determining the presence of a polymorphism in NAD(P)H oxidase in the patient, correlating the levels of HDL and the presence of the polymorphism with the increased risk of the coronary event, and outputting information indicative of the increased risk to an output device. In some embodiments, this method additionally comprises determining the serum CRP level in the patient and determining the serum total cholesterol level in the patient. Thus, the correlation step may also involve correlating the serum CRP level and the serum total cholesterol level, in combination with the HDL level and presence of the polymorphism, to determine that there is an increased risk of a coronary event.

In certain embodiments, patients having elevated apoA1 levels may further increase the risk of a coronary event for the patient. Thus, some embodiments further comprise determining that the patient has an elevated apoA1 level and correlating the elevated apoA1 level with a further increased risk of the coronary event. In some embodiments, the elevated apoA1 level is at least about 1.25 g/L. In some embodiments, the elevated apoA1 level is at least about 1.3 g/L. In some embodiments, the elevated apoA1 level is at least about 1.35 g/L. In some embodiments, the elevated apoA1 level is at least about 1.4 g/L. In some embodiments, the elevated apoA1 level is at least about 1.45 g/L. In some embodiments, the elevated apoA1 level is at least about 1.5 g/L. In some embodiments, the elevated apoA1 level ranges from about 1.25 to about 1.7 g/L.

In some embodiments, a normal elevated serum glucose level is a level of serum glucose equal to or less than about 4.8 mmol/L. In some embodiments, a normal serum glucose levels is a level of serum glucose less than or equal to about 4.6 mmol/L. In some embodiments, a normal serum glucose level is a level of serum glucose less than or equal to about 4.4 mmol/L. In some embodiments, a normal serum glucose level is a level of serum glucose less than or equal to about 4.3 mmol/L. In some embodiments, normal serum glucose levels comprises a level of serum glucose less than or equal to about 4.2 mmol/L.

In some embodiments, an elevated serum glucose level is a level of serum glucose greater than about 4.8 mmol/L. In some embodiments, an elevated serum glucose level is a level of serum glucose greater than or equal to about 4.9 mmol/L. In some embodiments, an elevated serum glucose level is a level of serum glucose greater than or equal to about 5 mmol/L. In some embodiments, an elevated serum glucose level is a level of serum glucose greater than or equal to about 5.2 mmol/L. In some embodiments, an elevated serum glucose level is a level of serum glucose greater than or equal to about 5.5 mmol/L. In some embodiments, an elevated serum triglyceride level is a level of serum triglyceride greater than or equal to about 5.7 mmol/L.

In some embodiments, an elevated serum triglyceride level is a level of serum triglyceride greater than or equal to about 1.7 mmol/L. In some embodiments, an elevated serum triglyceride level is a level of serum triglyceride greater than or equal to about 1.9 mmol/L. In other embodiments, an elevated serum triglyceride level is a level of serum triglyceride greater than or equal to about 2.1 mmol/L. In some embodiments, an elevated serum triglyceride level is a level of serum triglyceride greater than or equal to about 2.3 mmol/L. In some embodiments, an elevated serum triglyceride level is a level of serum triglyceride greater than or equal to about 2.5 mmol/l. In some embodiments, an elevated serum triglyceride level is a level of serum triglyceride greater than or equal to about 2.6 mmol/l.

The presence of certain markers within a patient, identified as having an increased risk of a coronary risk with one of the methods described herein, may further increase the likelihood or risk of the coronary event in the patient. For example, a patient who has an increased risk of a coronary event due to elevated level of serum triglyceride and a normal level of serum glucose, may be at a further increased risk of a coronary event if the patient also has an elevated level of fibrinogen in a body fluid. Fibrinogen is a glycoprotein that is involved in the clotting of blood. In response to an enzymatic cascade, it is converted to fibrin by the action of thrombin in the presence of ionized calcium.

Thus, one embodiment of a method for identifying an increased risk in a patient with an elevated level of serum triglyceride and a normal level of serum glucose, comprises determining that the patient has elevated levels of fibrinogen, correlating the level of fibrinogen with an increased risk of a coronary event, and outputting information indicative of an increased risk of a coronary event to an output device.

In some embodiments, an elevated level of fibrinogen is a level of fibrinogen greater than about 3.2 g/L. In some embodiments, an elevated level of fibrinogen is a level of fibrinogen greater than about 3.3 g/L. In some embodiments, an elevated level of fibrinogen is a level of fibrinogen greater than about 3.4 g/L. In some embodiments, an elevated level of fibrinogen is a level of fibrinogen greater than about 3.5 g/L. In some embodiments, an elevated level of fibrinogen is a level of fibrinogen greater than about 3.6 g/L.

In patients who have an increased risk of a coronary event due to elevated levels of serum triglycerides and normal levels of serum glucose, an elevated BMI may further increase the risk of a coronary event. BMI is generally used as a measurement of body fat based on the relationship between a person's height and weight. The BMI is calculated as weight in kg divided by height (in meters) squared (i.e. $kg/m^2$). One embodiment of a method of identifying an increased risk for a coronary event in a patient with an elevated level of serum triglyceride and a normal levels of serum glucose, comprises determining that the patient has an elevated BMI, correlating the elevated BMI with an increased risk of a coronary event, and outputting information indicative of an increased risk of a coronary event to an output device.

In some embodiments, an elevated BMI is a level of BMI greater than about 25 $kg/m^2$. In some embodiments, an elevated BMI is a level of BMI greater than about 25.5 $kg/m^2$. In some embodiments, an elevated BMI is a level of BMI greater than about 26 kg/m². In some embodiments, an elevated BMI is a level of BMI greater than about 26.4 kg/m². In some embodiments, an elevated BMI is a level of BMI greater than about 26.6 kg/m².

In some embodiments, the presence of both an elevated level of fibrinogen and an elevated BMI may further increase the risk of a coronary event in a patient who otherwise has a normal serum glucose level but an elevated level of serum triglycerides. One embodiment of a method for identifying an increased risk in a patient with an elevated level of serum triglyceride and a normal level of serum glucose comprises determining that the patient has an elevated level of fibrinogen, determining that the patient has an elevated BMI level, correlating the levels of fibrinogen and BMI with an increased risk of a coronary event, and outputting information indicative of an increased risk of a coronary event to an output device.

In some embodiments, a method for identifying an increased risk of a coronary event in a patient with an elevated serum triglyceride level and a normal serum glucose level, comprises receiving inputs to a processing module, the inputs comprising data indicative of one or more of an elevated fibrinogen level and an elevated BMI level. This method further comprises correlating the inputs in the processing module to determine that the patient has the increased risk of the coronary event and outputting information indicative of the increased risk to an output device.

In some embodiments, a system for identifying an increased risk of a coronary event in a patient comprises an input module and a processing module. In some embodiments, the input module receives inputs, the inputs comprising data indicative of a normal serum glucose level and an elevated serum triglyceride level in the patient. The processing module may correlate the levels of serum glucose and triglyceride to determine that the patient has the increased risk of the coronary event. Further embodiments may also include an output module that outputs information indicative of an increased risk of a coronary event.

Some embodiments of such systems can include input modules which receive data indicative of one or more of an elevated level of fibrinogen and an elevated level of BMI. In these embodiments, the processing module may correlate the one or more of elevated levels of fibrinogen and BMI. Further embodiments may include an output module that outputs information indicative of an increased risk of a coronary event.

Additional methods and systems as described herein may further relate to identifying an increased risk in a patient with metabolic syndrome. In some patients, the glucose level ranges from about 4.5 mmol/L to about 6 mmol/L. In some patients, the triglyceride level ranges from about 1.5 mmol/L to about 5 mmol/L. According to some embodiments, an increased level of serum PAI-1 may increase the risk of a coronary event in the patient. Thus, according to some embodiments, one method for identifying an increased risk of a coronary event in a patient having an elevated serum glucose level and an elevated serum triglyceride level comprises determining that the patient has an elevated PAI-1 level, correlating the elevated PAI-1 level with the increased risk of the coronary event, and outputting information indicative of the increased risk to an output device. In some embodiments, the elevated PAI-1 level is greater than about 40 µg/L. In some embodiments, the elevated PAI-1 level is greater than about 45 µg/L. In some embodiments, the elevated PAI-1 level is greater than about 47 µg/L. Some of the patients, according to his method, have metabolic syndrome.

It is also recognized that type II diabetes plays a role in coronary heart disease. For example, type II diabetics have an increased risk of recurrent MI compared to non-diabetic patients, and they are also more at risk to die from a subsequent MI than are non-diabetics. Diabetes results in a host of physiologic effects stemming from the body's inability to properly manage blood glucose levels. In addition to high blood glucose, these can include, but are not limited to, long term effects on blood vessel structure, effects on the renin-angiotensin-aldosterone system, evidence of chronic low-grade inflammation, oxidative stress, endothelial dysfunction, hypercoagulation, decreased fibrinolysis, and platelet hyperactivation.

Platelet hyperactivation plays a significant role in the development of vascular thrombosis. Hyperactivation is related to multiple steps in the pathway of platelet activation. One of the earliest and most crucial of these is the tethering of platelets to collagen of damaged epithelium by simultaneous binding of von Willebrand factor (vWF) to collagen and to platelet glycoprotein-Ib-IX-V (GpIb) complex. The Gp-Ib complex is composed of four subunits (GP Ibαa, GP-Ibβb, GPIX, GPV) with the binding site for vWF located on the N-terminus of the GP-Ibαa subunit.

As discussed above, diabetics have an increased risk for coronary events. At least some of the risk can be reasonably attributed to alterations in the inflammatory response system that occur as a result of diabetes. For example, in a recent study, vWF was found to be increased in diabetic relative to non-diabetic patients (Zerba et al., Thromb. Haemost. 86: 791-799, 2001, the entirety of which is hereby incorporated by reference herein). As vWF is involved in the blood-clotting enzymatic cascade, its increase level in diabetics suggests a direct link to the increased risk of future coronary events. Further, as vWF binds to receptors on the platelet surface, it is likely that variants in the vWF receptor, for example the vWF binding subunit Gp-Ibα, might affect the risk created by increased vWF levels in diabetics.

Accordingly, in some embodiments, a system for identifying increased risk of a coronary event in a patient comprises an input module and an output module, where in the input module receives input comprising data indicating the genotype of a patient with respect to a Gp-Ibα polymorphism. In particular, the polymorphism comprises the presence in the genetic code of the patient, at codon 145 of the Gp-Ibα protein coding sequence, a codon specifying either Thr or Met at residue 145 of the Gp-Ibα protein. Thus, in some embodiments, patients can be identified as being TT (homozygous for the T145 variant), MM (homozygous for the M145 variant) or TM (heterozygous, having one T allele and one M allele). In patients who are diabetic, the presence of the M allele will be predictive of a significantly increased risk of a recurrent coronary event, and the system will accordingly output a risk value taking into account the multiplicative nature of various numbers of risk factors. For example, in some embodiments, the system will output a value predictive of the risk of a recurrent coronary event for a patient with zero risk factors. For example, in some embodiments, the system will output a value predictive of the risk of a recurrent coronary event for a patient with one risk factor. For example, in some embodiments, the system will output a value predictive of the risk of a recurrent coronary event for a patient with two risk factors. For example, in some embodiments, the system will output a value predictive of the risk of a recurrent coronary event for a patient with three risk factors. In some embodiments, the patient will be diabetic. In some embodiments, the patient will be non-diabetic. In some embodiments, the patient will be pre-diabetic.

Some embodiments include a method of identifying or estimating risk of a medical outcome in a population and a subpopulation of patients. As before, the risk of a medical outcome (for example a coronary event) can be determined in a population by mapping a set of data points in a database in which each data point comprises values for n risk factors, as well as a corresponding outcome value. In some embodiments n=2, and the corresponding outcome value will be the occurrence of a particular medical outcome, for example a coronary event. In some embodiments a map is produced by mapping in 2 dimensions using the risk factor values as x and y values, with the z-axis values defined by the associated outcome value, which is typically coded as 0 (non-occurrence) or 1 (occurrence) with respect to the event that the associated outcome value represents.

The map so produced will reveal areas of relatively increased or decreased risk of the event of interest. These areas define one or more subpopulations with the main population. Data points within subpopulations can then be re-evaluated using a different set of risk factors in order to ascertain a second level of subpopulation, within an original subpopulation, for which risk can be attributed to the additional risk factors. Thus, embodiments of this method provide a way in which to successively analyze the relative contribution of various factors to risk of the event of interest, once an at risk subpopulation has been identified. Thus, the method provides one way in which to evaluate the relative risk contribution of 3 or more factors in order to determine either a relative risk, or a probability of occurrence of a medical outcome, for example a coronary event.

The invention is further described in terms of the following studies which are intended for the purpose of illustration and enablement and not to be construed as in any way limiting the scope of the present disclosure.

EXAMPLE 1

Relationship between HDL, CRP and Risk of a Coronary Event

Study Population

In examining the relationship between HDL, CRP, and the risk of a coronary event, the study population comprised the 767 patients of the THROMBO study who were non-diabetic and had complete laboratory data. Recurrent coronary outcome events for this study were cardiac death, myocardial infarction (MI), or unstable angina, whichever occurred first, and average length of follow-up was 26 months.

Independent Variables

Blood markers on fasting sera were determined two months after index MI. Concentrations of apolipoprotein-B (apoB), total cholesterol (Chol), apolipoprotein-A1 (apoA1), high density lipoprotein cholesterol (HDL), triglyceride (Trig), LDL peak particle diameter (PPD), glucose (Glu), insulin (Ins), BMI, plasminogen activator inhibitor-1 (PAI-1), lipoprotein(a) (Lp(a)), C-reactive protein (CRP), von Willibrand factor antigen (vWF), fibrinogen (Fibr), D-dimer (D-dim), Factor VII (FVII), and Factor VIIa (FVIIa) were determined. Median HDL particle diameter was determined using gradient gel electrophoresis as described previously (Rainwater, Meth. Mol. Biol. 110: 137-51, 1998; herein incorporated by reference in its entirety).

Statistical Analyses

All statistical and graphical procedures were performed with Statistica 7.0 (StatSoft Inc., Tulsa, Okla.). Variables were age-adjusted using linear regression. Significant differences ($p<0.05$) in laboratory values between groups were assessed using the Mann-Whitney U-test; and significant variables contributing to time to outcome event were determined using Kaplan-Meier analysis (log-rank statistic, $p<0.05$) and the Cox multivariate proportional hazards regression model.

Factor Analysis

Our approach to factor analysis has been described previously in Corsetti et al., Atherosclerosis 171: 351-8, 2003, and in Corsetti et al., Atherosclerosis 177: 367-73, 2004, the contents of which are herein incorporated by reference. Briefly, we used factor analysis to reduce results of multiple blood markers to fewer composite variables (factors) that represent more fundamental physiologic relationships among subsets of variables based upon correlations of variables within factors. Each factor is identified with a basic physiologic process based upon the variables making up the factor with the measure of the contribution of a variable being its loading on the factor. Factors account for most of the variance in the original data. Factor analysis results were used in subsequent statistical analyses using factor scores, the actual values of each factor for each patient (Corsetti et al., Atherosclerosis 177: 367-73, 2004).

Graphical Analysis

A graphical screening technique for identification of high-risk subgroups has been described previously in Corsetti, et al. Atherosclerosis 183: 293-300, 2005, which is herein incorporated by reference in its entirety. Briefly, three-dimensional scatter plots of patients, without and with outcome events, coded as 0 or 1, respectively, are generated as a function of two blood marker risk variables. To facilitate recognition of high-risk subgroups, concentrations are transformed to rankings (smallest concentration is assigned the value, 1) to more evenly distribute patient points over the x-y bivariate domain. Then, resulting points are smoothed to produce a three-dimensional surface map with height over the x-y plane becoming a measure of outcome prevalence over the bivariate blood marker domain. Potentially high-risk subgroups are identified as peaks and confirmed as such by subsequent statistical analyses. Demarcation of peaks is carried out by estimation from surface and contour plots of the isoprevalence contour line corresponding to increasing slope in comparison to surrounding relatively flat areas. Smoothing is useful to locate potentially high-risk populations, which can then be more rigorously analyzed statistically.

In some embodiments, the graphical screening technique can be used to determine a risk of an outcome of a particular event. A database comprising values for risk factors is used, as well as a corresponding outcome value, is used, as described above, to produce a graphic map. Where two risk factors are analyzed, the map will be a three-dimensional map comprising of risk factor value defining the x-y space, and the outcome value defining the z-space. Using more advanced calculation techniques, embodiments of the method can analyze more than two risk factors, for example three or four risk factors can be analyzed.

An advantage of the present method is that once the surface map is constructed, it provides a template onto which query data points can be placed, in order to determine an estimate outcome prevalence. For example, a patient can be assayed for two or more blood markers known to be potential risk factors. The values for these markers can then be used to define the values for the query data point. Those values can then be plotted on the surface map and an estimated outcome value can then be derived as being equal to the outcome value at that point on the surface map. The relative risk of the event will be generally given by the derived outcome value divided by the average outcome value, and that value can be outputted to a device as a risk factor.

In some embodiments, risk factors that can be analyzed include, but are not limited to, two or more of blood levels of apoA1, apoB, total serum cholesterol, HDL, cholesterol, triglyceride, glucose, insulin, plasminogen activator inhibitor-1, lipoprotein (a), C-reactive protein, von Willibrand factor antigen, fibrinogen, D-dimer, Factor VII, Factor VIIa, lipoprotein-associated phospholipase $A_2$, LDL peak particle diameter, type II diabetes, pre-diabetic syndrome, metabolic syndrome, a genetic polymorphism in NAD(P)H oxidase, a genetic polymorphism in Glycoprotein-Ibα, obesity, body mass index, and a previous myocardial infarction.

High-Risk Subgroup Validation

Confirmation of high-risk in patients contained in peaks relative to remaining patients was performed using Kaplan-Meier plots and Cox analysis with adjustment of clinical covariates performed by single entry ($p<0.1$) of sex, race, smoking, prior MI, index infarct type by ECG (Q-wave versus non-Q-wave), pulmonary congestion, ejection fraction during index MI, and claudication. Significant clinical covariates were retained in a subsequent model that included addition of the binary variable denoting subgroup membership ($p<0.05$) to confirm high-risk in the subgroup relative to remaining patients.

Within-Subgroup Risk Factors

To assess additional risk within a subgroup, Cox regression was applied to the subgroup using the 17 laboratory markers as independent variables with adjustment of clinical covariates within the subgroup performed as described above. Blood markers were dichotomized in three ways: quartile with highest concentration versus combined three quartiles with lower concentrations, combined two quartiles with highest concentrations versus combined two quartiles with lower concentrations, and combined three quartiles with highest concentrations versus quartile with lowest concentration. Separate univariate models were run for each laboratory variable dichotomized in the three ways described above. Then, a multivariate model adjusted for clinical covariates was run with simultaneous entry of all univariate significant laboratory values ($p<0.05$). Lastly, assessment of medication effects was performed by single entry into the resulting model of the following medications: statins, beta blockers, aspirin, calcium channel blockers, nitrates, ACE-inhibitors, and oral anticoagulants ($p<0.05$).

High-Risk Subgroup Identification

Clinical and laboratory characterization of the study population (N=767) have been given previously (Corsetti, et al. Atherosclerosis 183: 293-300, 2005) as well as factor analysis results (Corsetti et al., Atherosclerosis 171: 351-8, 2003; Corsetti et al., Atherosclerosis 177: 367-73, 2004). Summarizing factor analysis results, there were five factors that together with factor identification and blood marker contributions were ranked in decreasing order with respect to contribution to the total variance: cholesterol-lipoprotein (cholesterol, apoB, apoAI, HDL), inflammatory (CRP, fibrinogen, D-dimer, vWF), coagulation (Factor VII, Factor VIIa), dyslipidemia (PPD, triglycerides, HDL), and glycemia (glucose, insulin).

Of the two lipoprotein factors (cholesterol-lipoprotein and dyslipidemia), the cholesterol-lipoprotein factor accounted for the higher proportion of original laboratory data variance. Thus, to assess inflammation-lipoprotein interactions, a surface map of estimated prevalence of recurrent coronary events as a function of factor score ranks of the inflammation and cholesterol-lipoprotein factors was generated and is shown in FIG. 1. The plot shows a well-defined single peak at simultaneously high values of lipoprotein-cholesterol and inflammation and relatively little risk for either high values of lipoprotein-cholesterol or inflammation alone.

We also wanted to assess whether there might be similar results with single blood markers representing the two factors for more direct clinical relevance. Thus, a surface plot, shown in FIG. 2, of estimated prevalence versus total cholesterol and CRP was produced, the highest loading markers of the cholesterol-lipoprotein and inflammation factors, respectively. The plot shows a somewhat less well-defined peak, but nevertheless, a peak of high prevalence at simultaneously high values of total cholesterol and CRP and less risk for either high values of total cholesterol or CRP alone.

High-Risk Subgroup Validation

Figure 2:
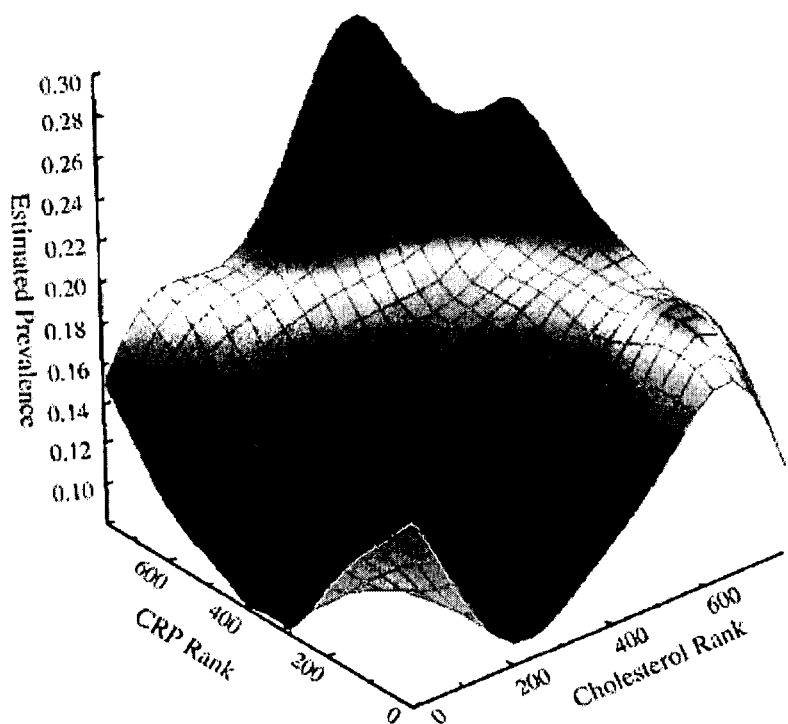
FIG. 2 is a surface map of estimated prevalence of recurrent coronary events as a function of cholesterol and CRP ranks in non-diabetic post-infarction patients.

Inspection of the peak in the plot of FIG. 2 and at various additional orientations demonstrated the base of the peak arose at an estimated prevalence of approximately 0.19. Thus, this value was chosen as the isoprevalence contour, values above which were taken to define a high-risk subgroup. By this definition, in FIG. 3 the corresponding contour plot with the isoprevalence line set at 0.19 shows a high-risk subgroup as a triangular region including 149 patients. The remaining 618 patients were thus designated as a low-risk patient subgroup. For reference, FIG. 3 gives Adult Treatment Panel III (ATP III) cut-points for cholesterol and CRP as well as lowest concentrations of the markers in the high-risk subgroup.

Figure 4:
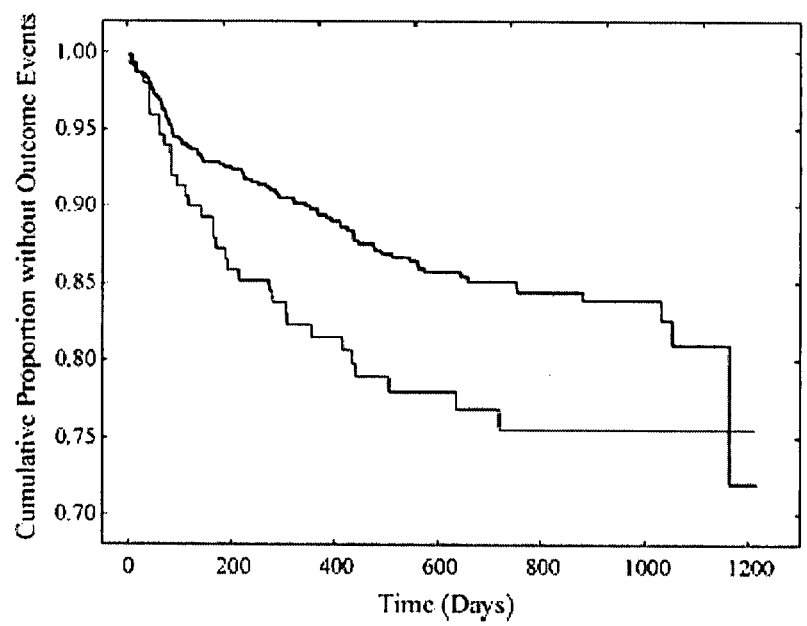
FIG. 4 is a graph of Kaplan-Meier curves of patients in high-risk subgroup versus lower risk subgroup.

To validate that the high risk subgroup was indeed subject to high risk of an event, Kaplan-Meier and Cox regression analyses were performed on both the high risk (N=149) and low-risk (N=618) subgroups. FIG. 4 shows Kaplan-Meier curves corresponding to the presumptive high-risk subgroup and lower risk subgroup. Analysis shows the groups to be statistically different (log-rank statistic, p=0.024). Additionally, Cox regression analysis adjusted for clinical covariates previously shown to be significant in the total population (prior MI, ejection fraction, and myocardial index), gave a hazard ratio for recurrent coronary events of 1.55 for the high risk subgroup (95% CI; 1.04, 2.31; p=0.033) relative to the low risk subgroup (Corsetti, et al., Atherosclerosis 183: 293-300, 2005). Thus, there was a 55% greater chance for a recurrent coronary event for a patient in the high-risk subgroup relative to a patient in the lower risk subgroup.

High-Risk Subgroup Characterization

Table 1 provides clinical and laboratory characteristics of low and high-risk subgroups. Both groups demonstrated similar clinical characteristics except for a higher proportion of females in the high risk subgroup. In addition to the expected higher cholesterol and CRP, there were significantly higher values observed in the high risk subgroup for other markers of lipoprotein-cholesterol (apoB, apoAI) and inflammation factors (fibrinogen, D-dimer, vWF). Additionally, the high-risk subgroup displayed higher values for triglycerides, PAI-1, and factor VII.

We further characterized the high-risk subgroup with regard to recurrent coronary events, by comparing clinical and laboratory results for patients with and without outcome events. Both groups showed similar clinical and laboratory characteristics with the only difference being higher levels of HDL in event positive patients (1.14±0.38 mmol/L compared to 1.01±0.25 mmol/L; p<0.05, Mann-Whitney U).

TABLE 1

Clinical and Laboratory Characterization of Low-Risk and High-Risk Subgroups

| Characteristic | Low Risk; n = 618 (Mean ± S.D.) | High-Risk; n = 149 (Mean ± S.D.) |
| --- | --- | --- |
| Outcome Event Rate (%) | 14.4 | 22.1 |
| Age (Years) | 58.4 | 58.0 |
| Males/Females (%) | 80.3/19.7 | 63.8/36.2 |
| Race (% Caucasian) | 79.9 | 72.5 |
| Prior MI (%) | 16.9 | 16.3 |
| Statins (%) | 42.7 | 30.2 |
| Beta Blockers (%) | 78.2 | 75.8 |
| Aspirin (%) | 83.1 | 77.2 |
| Ca Channel Blockers | 20.6 | 16.8 |
| Nitrates (%) | 32.4 | 38.9 |
| ACE Inhibitors (%) | 31.4 | 41.6 |
| Oral Anticoagulants (%) | 16.2 | 24.8 |
| Cholesterol (mmol/L) | 4.86 ± 1.02 | 6.10 ± 1.07* |
| CRP (mg/L) | 2.90 ± 4.50 | 10.3 ± 10.7* |
| ApoB (g/L) | 1.18 ± 0.26 | 1.42 ± 0.27* |
| ApoA1 (g/L) | 1.16 ± 0.24 | 1.27 ± 0.25* |
| HDL (mmol/L) | 0.98 ± 0.28 | 1.03 ± 0.29 |
| Triglyceride (mmol/L) | 2.13 ± 1.22 | 2.71 ± 1.49* |
| LDL-PPD (nm) | 26.3 ± 0.83 | 26.17 ± 0.80 |
| Glucose (mmol/L) | 4.94 ± 1.08 | 5.16 ± 1.50 |
| Insulin (pmol/L) | 119 ± 178 | 124 ± 117 |
| BMI (kg/m$^2$) | 27.4 ± 4.66 | 28.2 ± 5.70 |
| PAI-1 (ug/L) | 25.4 ± 22.8 | 31.7 ± 30.6* |
| Lp (a) (mmol/L) | 0.62 ± 0.58 | 0.65 ± 0.62 |
| vWF (%) | 137 ± 58.6 | 163 ± 70* |
| D-dimer (ug/L) | 457 ± 411 | 537 ± 428* |
| Fibrinogen (g/L) | 3.31 ± 0.67 | 4.14 ± 1.00* |
| Factor VII (%) | 99.1 ± 39.2 | 116.5 ± 54.2* |
| Factor VIIa (ug/L) | 2.44 ± 1.53 | 2.87 ± 2.23 |
| HDL-Med (nm) | 8.79 ± 0.29 | 8.79 ± 0.27 |

*Difference significant by Mann-Whitney U test (p < 0.05).

Additional Risk Within the High-Risk Subgroup

To elucidate the source of risk within the high-risk subgroup, especially in view of finding higher HDL levels in event positive patients, Cox regression and Kaplan-Meier analyses were performed as a function of the original 17 laboratory parameters within the high-risk subgroup. For Cox analyses, laboratory parameters were dichotomized in three ways as described above. Of the eight clinical covariates, only pulmonary congestion gained entry (p<0.1). Adjusting for pulmonary congestion, single entry into the model of each of the 17 laboratory parameters was performed separately for each of the three dichotomization schemes. Results showed only one marker to enter the model and in only one way. This was HDL dichotomized as quartile with highest concentration versus combined three quartiles with lowest concentrations. Results gave for elevated HDL a hazard ratio of 2.24 (95% CI; 1.12, 4.49; p=0.023). Subsequent single entry of medications demonstrated no effect. The corresponding Kaplan-Meier curves for highest HDL concentration quartile versus combined three lowest quartiles are given in FIG. 5 which shows higher rate of outcome events for patients in the highest HDL quartile (log-rank statistic, p=0.012). Interestingly, this effect seems essentially complete within 1 year. To further characterize patients of the highest HDL quartile in comparison to patients in the combined three lowest quartiles of HDL, the highest quartile HDL patients demonstrated statistically significant differences in blood markers including higher apoA1 levels (1.48±0.23 g/L compared to 1.20±0.22 g/L), and a larger HDL particle size (8.98±0.30 nm compared to 8.73±0.23 nm).

As a control experiment, we assessed the role of blood markers, especially HDL, in the low-risk subgroup (N=618) using Cox regressions adjusted for significant clinical covariates (prior MI and myocardial index) and the blood markers dichotomized in the same three ways. Only BMI, dichotomized as quartile with highest values versus combined three quartiles with lowest values, entered the model giving a hazard ratio of 1.63 (95% CI; 1.05, 2.51; p=0.028). There were no significant medication effects. Although HDL did not enter the model, closest approach p=0.105) gave a hazard ratio for elevated HDL of 0.64 suggesting high levels of HDL are protective against recurrent coronary events in this subgroup.

This study demonstrated the presence of a subgroup of patients at high risk for recurrent coronary events in a population of non-diabetic postinfarction patients. The high-risk subgroup was characterized by concomitantly high levels of CRP and total cholesterol. High risk in the subgroup was a manifestation of the interaction of the risks associated with inflammation and hypercholesterolemia. Further analysis within the high-risk subgroup demonstrated only HDL to be an independent and significant predictor of risk within the subgroup from a collection of metabolic, inflammatory, and thrombogenic blood markers. Furthermore, HDL-associated risk within the subgroup was associated with high, not low, levels of HDL. Additionally, patients with the higher levels of HDL were found to have larger diameter HDL particles as well as higher levels of apoAI.

Results indicate that determining both CRP and total cholesterol levels identify high-risk postinfarction patients. This is consistent with the known poor correlation of CRP and blood lipid levels seen in other work in populations at risk for a first myocardial infarction and in the present study as demonstrated by the presence of CRP and total cholesterol in separate factors that are actually formulated in a way so as to minimize inter-factor correlations (Ridker et al., Circulation 97: 2007-11, 1998; Ridker et al., N. Engl. J. Med. 347: 1557-65, 2002; both of which are incorporated herein by reference).

Poor correlation between CRP and atherogenic lipid levels makes possible individual contributions to total risk that may be more than multiplicative (Ridker et al., Circulation 97: 2007-11, 1998; incorporated herein by reference). With particular regard to postinfarction patients (reviewed by Bassuk et al., Curr. Probl. Cardiol. 29: 439-93, 2004; incorporated herein by reference), evidence for CRP-associated risk of recurrent events is less consistent than in the setting of primary prevention. Our results indicate that inflammatory processes in postinfarction patients as represented by increased CRP levels are indeed important in predicting risk. Lack of similar findings in other studies of postinfarction patients may relate to use of traditional risk factor stratification.

In contrast, the graphical screening approach used in our study for identification of high-risk subgroups allowed delineation of a subgroup with high levels of CRP and total cholesterol that because of its shape in the outcome prevalence map could not be characterized by single cut point values for either CRP or cholesterol.

Results regarding additional risk for recurrent coronary events within the high-risk subgroup defined by high cholesterol and CRP levels singled out only HDL as a statistically significant predictor of risk within the subgroup, and surprisingly, risk was associated with higher rather than lower levels of HDL. Further, higher risk patients within the subgroup had larger HDL particles and higher apoA1 concentrations than lower risk patients having lower concentrations of HDL. These findings may indicate that for the presumably cholesteryl ester-rich HDL particles in higher risk patients, there is a relative inability to effectively support reverse cholesterol transport.

The high-risk subgroup identified in our study has an inflammatory component as demonstrated by elevated CRP levels. Additionally, there is further within-subgroup risk associated with high levels of HDL. Without being bound to any particular theory, CVD risk in association with high HDL may be connected with the role of HDL in inflammation, or more specifically, with changing in the function of HDL from an anti-inflammatory agent to a pro-inflammatory agent. This change may arise from inflammation-induced alterations in HDL particles, or by displacement and/or modification of multiple protein constituents of HDL including apoA1, lecithin: cholesterol acyltransferase, paraoxonase, and lipoprotein-associated phospholipase A2 (platelet-activating factor acetylhydrolase).

Thus, a subgroup of patients at high risk for recurrent coronary events in a study population of non-diabetic postinfarction patients can be identified by using an exploratory graphical approach to map outcome event prevalence. The subgroup derived from interaction of atherogenic lipoprotein associated risk, in this case—hypercholesterolemia, and inflammation—associated risk as manifested by high levels of CRP. Additionally, within the high-risk subgroup and from a set of lipoprotein, metabolic, inflammatory, and thrombogenic blood markers, only high HDL was found to be a significant and independent predictor of risk.

EXAMPLE 2

Relationship Between Genetic Variants of p22phox and Risk of a Coronary Event

Study Population

In this example, the initial study population comprised 663 patients of the THROMBO study who were non-diabetic and who had complete blood marker laboratory data and C242T (NAD(P)H oxidase p22phox) genotyping. Recurrent coronary outcome events were cardiac death, myocardial infarction (MI), or unstable angina (hospitalization during follow-up with an increase in either frequency or duration of angina symptoms or with development of new angina at rest with both requiring ischemic ECG changes without enzyme elevation), whichever occurred first. Average patient follow-up was 26 months.

Blood Markers

Blood marker levels on fasting sera drawn two months after index MI were determined as described previously (Moss et al., Circulation 99: 2517-2522, 1999) for: apolipoprotein B (apoB), total cholesterol, apoA1, HDL, triglyceride, LDL peak particle diameter (LDL-PPD), glucose, insulin, BMI, plasminogen activator inhibitor-1 (PAI-1), lipoprotein(a) (Lp (a)), C-reactive protein, von Willibrand factor antigen (vWF), fibrinogen, D-dimer, factor VII, and factor VIIa. Gradient gel electrophoresis was used to determine median HDL particle diameter (HDL-Med) and HDL particle subfractionation according to size as described previously (Rainwater, Meth. Mol. Biol. 110: 137-151, 1998; the entirety of which is incorporated by reference herein).

Genotyping

Genotyping for p22phox (CYBA) H72Y SNP (SNP ID: RS4673) was performed by melting curve analysis (Light Cycler, Roche Diagnostics, Indianapolis, Ind.) based on G-nucleobase quenching using a 3'-FAM labeled probe to distinguish the reference sequence (T nucleotide in codon 72; T allele) and variant sequence (C nucleotide in codon 72; C allele). Whether a T or C is present at the relevant location in codon 72 dictates the amino acid residue encoded. The T allele encodes a Tyr residue at residue 72, while the C allele encodes a protein having a His residue (Inoue et al., Circulation 98: 135-137, 1998; Guzik et al., Circulation 102: 1744-1747, 2000; both of which are herein incorporated by reference in their entireties). Individuals will be homozygous for either the T allele (TT individuals), the C allele (CC individuals) or will be heterozygous at this locus (CT individuals).

The variant allele frequency in our population (0.63) was consistent with previously published reports. The population was not in Hardy-Weinberg equilibrium with respect to the polymorphism (observed: CC-0.416, CT-0.418, and TT-0.166 versus expected: CC-0.391, CT-0.469, and TT-0.141; p=0.005) possibly reflecting a selection effect for the T allele. Stratification according to race revealed for whites a result essentially the same as above; whereas for blacks Hardy-Weinberg equilibrium was attained.

Statistical Analyses

As in Example 1, the statistical and graphical analyses were performed with Statistica 7.0. Linear regression was used to adjust variables for age. Significant differences between pairs of population medians were assessed using Mann-Whitney U test ($p<0.05$) while Kruskal-Wallis ($p<0.05$) was used for comparisons of more than two groups. Chi-square tests ($p<0.05$) were used for comparison of proportions and genotypic distributions. Analysis of recurrent coronary events over time was performed using Kaplan-Meier analysis with log rank statistic ($p<0.05$) used for determining significant differences between curves.

The time to a recurrent coronary event was followed using Cox proportional-hazards models. Blood markers were treated as binary variables dichotomized according to quartile with highest levels versus combined three quartiles with lowest levels; and genotype variants were treated as binary variables. Adjustment for significant ($p<0.10$) clinical covariates was performed by evaluation of: sex, race, smoking, prior MI, myocardial index (infarct type by ECG, Q-wave versus non Q-wave), pulmonary congestion, ejection fraction (EF; $>0.30$, $\leq 0.30$), and claudication. Univariate models were then run for blood markers. A complete multivariate model adjusted for significant clinical covariates was then run with simultaneous entry of all univariate significant blood marker variables ($p<0.05$) and both polymorphisms. Assessment of medication effects was performed by single entry into the multivariate model of: statins, beta blockers, aspirin, calcium channel blockers, nitrates, ACE-inhibitors, and oral anticoagulants ($p<0.05$).

Three-dimensional plots of estimated prevalence of recurrent coronary events as a function of cholesterol and CRP ranks were used to identify high-risk patient subgroups. Briefly, scatter plots of patients, without and with recurrent events, coded as 0 and 1 respectively, were generated as a function of two blood marker risk variables transformed to ranks to more evenly scatter points over the bivariate risk domain and then smoothed to produce a 3-dimensional surface map with height over the x-y plane serving as an estimate of outcome prevalence.

Clinical and laboratory characterization of the initial study population of non-diabetic THROMBO patients for whom complete blood marker and genotypic results were available (N=663) is given in Table 2 and is similar to results reported previously for the larger patient group having complete blood marker results (N=767; Corsetti, et al. Atherosclerosis 183: 293-300, 2005). Notable findings were that patients were overweight, 77.7% male; and 80.1% white. Markers with mean values elevated relative to standard reference ranges included triglycerides (2.26±1.30 mmol/L; normal <1.69 mmol/L), CRP (4.06±5.59 mg/L; normal <1.0 mg/l), and D-dimer (455±346 µg/L; normal <200 µg/L) while HDL was slightly decreased (1.00 mmol/L; normal ≥1.03 mmol/L).

TABLE 2

Clinical and Laboratory Characterization of Study Population

| Characteristic | Total N = 663 |
|---|---|
| Recurrent Events n (%) | 105 (15.8) |
| Age (Years) | 58.4 |
| Males (%) | 77.7 |
| Caucasian (%) | 80.1 |
| Prior MI (%) | 16.5 |
| Statins (%) | 39.7 |
| Beta Blockers (%) | 78.1 |
| Aspirin (%) | 81.4 |
| Calcium Channel Blockers (%) | 19.8 |
| Nitrates (%) | 34.1 |
| ACE Inhibitors (%) | 32.1 |
| Oral Anticoagulants (%) | 17.5 |
|  | Mean ± S.D. |
| ApoB (g/L) | 1.23 ± 0.28 |
| Cholesterol (mmol/L) | 5.13 ± 1.15 |
| ApoA1 (g/L) | 1.18 ± 0.25 |
| HDL (mmol/L) | 1.00 ± 0.28 |
| Triglyceride (mmol/L) | 2.26 ± 1.3 |
| LDL-PPD (nm) | 26.26 ± 0.82 |
| Glucose (mmol/L) | 5.02 ± 1.21 |
| Insulin (pmol/L) | 119 ± 164 |
| BMI (kg/m2) | 27.6 ± 4.88 |
| PAI-1 (ug/L) | 26.8 ± 24.6 |
| Lp(a) (mmol/L) | 0.62 ± 0.58 |
| CRP (mg/L) | 4.06 ± 5.59 |
| vWF (%) | 140 ± 61 |
| Fibrinogen (g/L) | 3.48 ± 0.8 |
| D-dimer (ug/L) | 455 ± 346 |
| Factor VII (%) | 102 ± 42 |
| Factor VIIa (ug/L) | 2.53 ± 1.71 |
| HDL-Med (nm) | 8.79 ± 0.27 |

C242T Polymorphism in NAD(P)H Oxidase p22phox Subunit in Total Population

Genotypic frequencies of individuals in the study population with respect to the p22phox polymorphism were: CC-41.6%, CT-41.8%, and TT-16.6%. Distribution of frequencies as a function of race (whites; CC-40.9%, CT-42.0%, and TT-17.1% and blacks; CC-44.7%, CT-40.9%, and TT-14.4%) were not statistically different (p=0.64). There were no significant differences in levels of laboratory markers as a function of C242T variant. Kaplan-Meier analysis for C242T dichotomization scheme gave results (plots not shown) for p-values as 0.10 for CT versus CC and 0.84 for CT versus TT indicating closer similarity of CT to TT regarding the likelihood of outcome events. Thus, dichotomization was performed as CC versus CT plus TT, consistent with recent studies (Shimoni et al., Isr. Med. Ass. J. 5: 705-06, 2003, incorporated herein by reference) and overall findings of the THROMBO study (Moss et al., Am. J. Cardiol. 96: 177-182, 2005, incorporated herein by reference). Based on this dichotomization, there were no significant differences in clinical markers including race. Among laboratory markers, only HDL median diameter was different (CC=8.82±0.29 nm compared to CT plus TT n=8.77±0.26 nm, p=0.038).

Interaction of Cholesterol and CRP

The interaction of hypercholesterolemia with inflammation as represented by CRP in development of recurrent coronary event risk is demonstrated by the estimated outcome prevalence contour map as a function of cholesterol and CRP (FIG. 6). The map shows a major high-risk peak at high levels of both cholesterol and CRP. The figure has superimposed on it isoprevalence lines (0.20) at the estimated base of the peak resulting in tentative classification of patients in a lower risk baseline subgroup (N=530) or a high-risk subgroup (N=103). Kaplan-Meier analysis confirmed increased recurrent coronary event risk in the presumptive high-risk subgroup relative to baseline (plot not shown, p=0.004).

Results of subgroup characterization are shown in Table 3. In comparison to baseline, patients in the high-risk subgroup had: higher percentage of recurrent outcome events (25.2 versus 14.1%), more females (31.1 versus 20.7%), more patients on oral anticoagulants (25.2 versus 16.1%); and higher levels of apoB (1.37±0.28 vs. 1.21±0.27 mmol/L), cholesterol (5.91±1.11 vs. 4.99±1.10 mmol/L), apoA1 (1.24±0.24 vs. 1.17±0.25 g/L), triglyceride (2.58±1.46 vs. 2.20±1.27 mmol/L), insulin (131±119 vs. 117±171 pmol/L), PAI-1 (32.2±30.1 vs. 25.8±23.3 µg/L), CRP (11.6±8.43 vs. 2.68±3.44 mg/L), vWF (166±71 vs. 135±58%), fibrinogen (4.26+0.94 vs. 3.34±0.68 g/L), D-dimer (604±512 vs. 428±298 µg/L), and Factor VII (112±50 vs. 100±41%).

TABLE 3

Clinical and Laboratory Characterization of Baseline and High-Risk Subgroups

| Characteristic | Baseline/N = 560 | High-Risk/N = 103 |
|---|---|---|
| Recurrent Events N (%) | 79 (14.1) | 26 (25.2)* |
| Age (years) | 58.3 | 58.6 |
| Males (%) | 79.3 | 68.9* |
| Race (% White) | 80.7 | 76.7 |
| Prior MI (%) | 16.7 | 15.7 |
| Statins (%) | 41.3 | 31.1 |
| Beta Blockers (%) | 78.6 | 75.7 |
| Aspirin (%) | 82.7 | 74.8 |
| Ca Channel Blockers (%) | 20.7 | 14.6 |
| Nitrates (%) | 33 | 39.8 |
| ACE Inhibitors (%) | 31.3 | 36.9 |
| Oral Anticoagulants (%) | 16.1 | 25.2* |
|  | Mean ± SD | Mean ± SD |
| ApoB (g/L) | 1.21 ± 0.27 | 1.37 ± 0.28* |
| Cholesterol (mmol/L) | 4.99 ± 1.10 | 5.91 ± 1.11* |
| ApoA1 (g/L) | 1.17 ± 0.25 | 1.24 ± 0.24* |
| HDL (mmol/L) | 1.00 ± 0.28 | 1.02 ± 0.26 |
| Triglyceride (mmol/L) | 2.20 ± 1.27 | 2.58 ± 1.46* |
| LDL-PPD (nm) | 26.27 ± 0.83 | 26.22 ± 0.8 |
| Glucose (mmol/L) | 4.99 ± 1.17 | 5.19 ± 1.41 |
| Insulin (pmol/L) | 117 ± 171 | 131 ± 119* |
| BMI (kg/m$^2$) | 27.49 ± 4.61 | 28.23 ± 6.1 |
| PAI-1 (µg/L) | 25.8 ± 23.3 | 32.2 ± 30.1* |
| Lp(a) (mmol/L) | 0.62 ± 0.58 | 0.64 ± 0.61 |
| CRP (mg/L) | 2.68 ± 3.44 | 11.55 ± 8.43* |
| vWF (%) | 135 ± 58 | 166 ± 71* |
| Fibrinogen (g/L) | 3.34 ± 0.68 | 4.26 ± 0.94* |
| D-dimer (µg/L) | 428 ± 298 | 604 ± 512* |
| Factor VII (%) | 100 ± 41 | 112 ± 50* |
| Factor VIIa (µg/L) | 2.48 ± 1.61 | 2.82 ± 2.15 |
| HDL-Med (nm) | 8.79 ± 0.28 | 8.80 ± 0.26 |

*Significant difference between baseline and high-risk subgroups (Mann-Whitney U or Chi-square, p < 0.05).

C242T Polymorphism in High-Risk Subgroup

Frequencies of the CC, CT, and TT genotypes as percentages of the population were: baseline—40.7%, 41.6%, and 17.7%; high-risk subgroup—46.6%, 42.7%, and 10.7%, respectively. There was no significant difference in variant distributions between subgroups (p=0.19). Frequency distributions within the high-risk subgroup were not different as functions of race (p=0.41) or gender (p=0.52).

C242T Polymorphism and Recurrent Coronary Event Risk

To assess the contribution of the C242T polymorphism to overall risk in the high-risk subgroup, an outcome prevalence map was generated containing only CC patients (FIG. 7; panel labeled A), with another map generated containing CT plus TT patients (FIG. 7; panel labeled B). The maps show greatest concentration of risk occurring in CC patients with high levels of both cholesterol and CRP and low risk in the corresponding region occurring in CT plus TT patients. Additionally, the high-risk region closely overlies the high-risk subgroup of FIG. 6. These findings suggest association of the CC variant with increased risk seen in the high-risk subgroup.

Recurrent Coronary Event Risk within High-Risk Subgroup

Further evaluation of the C242T polymorphism in development of risk within the high-risk subgroup involved Kaplan-Meier analysis, as shown in FIGS. 8A and 8B. Revealed is a significant CC-associated risk versus CT plus TT ($p=0.0073$) in the high-risk subgroup and no association with risk in baseline patients ($p=0.59$).

Risk within the high-risk subgroup was further examined using the Cox proportional hazards model adjusted for significant clinical covariates with blood markers and C242T as independent variables. Blood markers were treated as binary variables with dichotomization as highest concentration quartile versus combined three quartiles with lowest concentrations; C242T was treated as a binary variable with coding as follows: CC-1; CT plus TT-0. Univariate modeling ($p<0.05$) with Cox regression demonstrated that HDL and Lp(a) were significant blood markers. Clinical covariates were evaluated, with gender and pulmonary congestion found to be significant ($p<0.1$). Multivariate models adjusted for gender and presence of pulmonary congestion were then run with simultaneous entry of HDL, Lp(a), and C242T as independent variables. Results demonstrated entry of HDL and C242T into the model with overall fit having a p-value of 0.0012 and values for hazard ratios, 95% confidence intervals, and p-values as follows: HDL (2.62, 1.05-6.55, $p=0.039$), and CC versus CT plus TT (3.14, 1.34-7.35, $p=0.0084$). Medication effects were then evaluated by single entry of medications into the multivariate model. Only nitrates were found to be significant, but this did not affect HDL and C242T which also remained significant.

HDL Subfractionation in Baseline and High-Risk Subgroups

To elucidate the nature of risk-associated HDL, size dependent subfractionation of HDL was performed using gradient gel electrophoresis. Results are shown for baseline and high-risk subgroups for patients without and with recurrent coronary events (Table 4). FIG. 9 illustrates that only where the H2a subfraction corresponded to larger HDL particles were there differences observed The high-risk subgroup with outcomes had significantly higher levels of H2a cholesterol than the baseline subgroup without (*$p=0.018$) or with outcomes (†$p=0.003$) (Kruskal-Wallis).

TABLE 4

Cholesterol Concentrations (mmol) in HDL Subfractions for Baseline and High-Risk Subgroups as a Function of Recurrent Coronary Outcomes

| HDL Subfraction | Without Outcome (Mean ± S.D.) | With Outcome (Mean ± S.D.) |
| --- | --- | --- |
| Baseline | N = 481 | N = 79 |
| $H_{2b}$ | 0.247 ± 0.138 | 0.251 ± 0.190 |
| $H_{2a}$ | 0.223 ± 0.087 | 0.209 ± 0.081 |
| $H_{3a}$ | 0.249 ± 0.071 | 0.232 ± 0.063 |
| $H_{3b}$ | 0.156 ± 0.040 | 0.160 ± 0.041 |
| $H_{3c}$ | 0.086 ± 0.031 | 0.092 ± 0.029 |
| High-Risk | N = 77 | N = 26 |
| $H_{2b}$ | 0.230 ± 0.115 | 0.273 ± 0.128 |
| $H_{2a}$ | 0.232 ± 0.088 | 0.264 ± 0.099 |
| $H_{3a}$ | 0.238 ± 0.070 | 0.258 ± 0.082 |
| $H_{3b}$ | 0.155 ± 0.039 | 0.162 ± 0.051 |
| $H_{3c}$ | 0.092 ± 0.033 | 0.086 ± 0.028 |

In the present example, one aim was to determine the contribution of inflammation in the establishment of risk for recurrent coronary events associated with elevated HDL within a subgroup of postinfarction patients defined by high levels of total cholesterol and CRP. Thus, we examined the effect of the C242T polymorphism in NAD(P)H oxidase p22phox subunit within the subgroup. NAD(P)H oxidase is a key enzyme involved in initiation of multiple processes associated with atherogenesis, through its role as a major source of reactive oxygen species that in turn impact on multiple signaling pathways associated with vascular inflammation. Study results demonstrate the importance of inflammation-related processes in establishment of HDL-associated risk in that an increase within subgroup risk occurred in patients homozygous for the C allele relative to patients with the T allele.

Without wishing to be bound to any particular theory, we believe that altered HDL plays an important role in development of risk in the patient subgroup as disclosed herein. The role of oxidative changes in establishment of risk within the subgroup was underscored by finding risk associated with the C242T polymorphism of p22phox subunit of NAD(P)H oxidase in the context of polymorphism-associated functional differences in enzyme activity. Functional studies regarding C242T effects suggest, on balance, a protective role for the T allele (Soccio et al., Eur. J. Clin. Invest. 35: 305-314, 2005, incorporated herein by reference).

These results suggest that HDL-associated risk is a manifestation of inflammatory changes in HDL in view of importance of inflammation-associated oxidative changes that result in functional alterations of HDL. In particular, the T allele is found to be protective against coronary artery disease in men with hypercholesterolemia which is consistent with results for patients in the high-risk subgroup who were on average hypercholesterolemic.

In summary, these studies demonstrated that elevated HDL is a risk factor for recurrent coronary events in a subgroup of postinfarction patients defined by high levels of total cholesterol and CRP; and that the risk associated with elevated HDL is likely connected to inflammation given that high CRP is one of the defining characteristics of the subgroup. The role of inflammation was further supported by demonstrating higher risk for patients in the subgroup who were homozygous for the C allele of the C242T polymorphism of p22phox. Lower levels of inflammation-related intermediates have been reported in association with the T allele of this polymorphism.

EXAMPLE 3

The Relationship between Serum Glucose and Triglyceride Levels and Risk of a Coronary Event Study Population A description of the THROMBO study of post-myocardial infarction patients has been discussed above. In this example, diabetics were excluded from the 940 patients of the study, to yield a study population of 767 patients. None of the 767 patients of the study population were on glycemic control medications. Presence of metabolic syndrome (MS) was assessed using Adult Treatment Panel III (ATP III) criteria for MS slightly modified (use of BMI>28.8 kg/m² for obesity instead of waist circumference, and clinical history or treatment of hypertension instead of manometry) as described previously (Corsetti et al., Atherosclerosis 177: 367-73, 2004; herein incorporated by reference in its entirety). Coronary events were cardiac death, myocardial infarction (MI), or unstable angina, whichever occurred first. The average follow-up period was 26 months.

Laboratory Variables

Fasting blood samples were drawn 2 months after an index myocardial infarction. Concentrations of apolipoprotein-B (apoB), total cholesterol (Chol), apolipoprotein-A1 (apoA1), high density lipoprotein cholesterol (HDL), triglyceride (Trig), LDL peak particle diameter (PPD), glucose (Glu), insulin (Ins), BMI, plasminogen activator inhibitor-1 (PAI-1), lipoprotein(a) (Lp(a)), C-reactive protein (CRP), von Willibrand factor antigen (vWF), fibrinogen (Fibr), D-dimer (D-dim), Factor VII (FVII), and Factor VIIa (FVIIa) were determined as described in earlier examples.

Statistical Analyses

All statistical and graphical procedures were performed with Statistica 6.0 (StatSoft, Inc., Tulsa, Okla.). Variables were age-adjusted using linear regression. Significant differences ($p<0.05$) in laboratory values between subgroups in comparison to baseline patients were assessed using the Mann-Whitney U-test.

Graphical Analysis

As introduced above, a graphical screening technique has been developed to presumptively identify patient subgroups potentially at high risk for recurrent coronary events. The technique is based on three dimensional scatter plots with two laboratory parameters as independent variables in the x-y plane and outcome as dependent variable on the z-axis coded as present (1) or absent (0). High-risk subgroups present as regions in the x-y plane with higher proportions of z=1 points. Large fluctuations in outcome over small changes in independent variables make recognition of such regions difficult. To facilitate recognition of such regions, we used a surface-smoothing algorithm for noise reduction.

The result of this operation is a smooth surface extending over the x-y plane with surface height becoming, because of coding of outcome as 1 or 0, a measure of the proportion of patients in any x-y neighborhood with the event; that is, a measure of event prevalence. This approach produces a prevalence map over the bivariate domain of independent variables. It should be noted that smoothing facilitates recognition of trends in noisy data. However, it is not a regression and data are not being used to fit an equation or model. As such, this approach is not a rigorous statistical procedure, but rather a screening method with which to visualize otherwise non-obvious relationships between various risk factors. It is therefore used to locate potentially high-risk populations, with conclusive demonstration of high risk making subsequent use of rigorous statistical approaches. To facilitate smoothing in these studies, laboratory values were compacted for a more even distribution of points in the bivariate plane via transformation to ranks.

High-Risk Subgroup Validation

To confirm high risk in subgroups presumptively identified as such by graphical analysis, Kaplan-Meier plots and Cox proportional hazards models were used in comparing time to outcome event for each subgroup to that of baseline patients. Log rank statistic ($p<0.05$) was used to determine significant differences in the Kaplan-Meier plots. For Cox analysis, adjustment of clinical variables was first evaluated by single entry into the model $p<0.1$) of the following binary variables in the total population (N=767): sex, race, smoking, prior MI, index infarct type by ECG (Q-wave versus non Q-wave), pulmonary congestion, ejection fraction during index MI (>0.30/≤0.30/not obtained), and claudication. Significant clinical variables were retained in the model, and separately for each presumptive high-risk subgroup, a variable dichotomized according to whether a patient was a member of the given subgroup or baseline group was evaluated for entry into the model ($p<0.05$).

Risk Prediction within Individual Subgroups

To further investigate the risk within each subgroup, assessment of laboratory variables as predictors of risk was performed using the Cox model separately in each subgroup using as independent variables the 17 laboratory markers dichotomized within each subgroup in two ways: highest risk quartile of the laboratory values versus combined three lower risk quartiles, and combined two highest risk quartiles versus combined two lower risk quartiles. Separately for each high risk subgroup, a univariate model was run by single entry of each laboratory variable dichotomized both ways. Then a multivariate model was run with adjustment for significant clinical variables determined as described above and with simultaneous entry of all univariate significant laboratory values ($p<0.05$). Lastly, medication effects were assessed by single entry into the model of the following medications: beta blockers, aspirin, calcium channel blockers, nitrates, ACE inhibitors, oral anticoagulants, and statins ($p<0.05$).

Table 5 shows clinical characteristics and means and standard deviations of laboratory markers for the 767 patients comprising the study population. The table shows elevated triglyceride, elevated BMI to the overweight level, and low HDL (Expert Panel on the Identification, Evaluation, and Treatment of Overweight and Obesity in Adults; Arch. Int. Med. 158: 1855-1867, 1998; Expert Panel on Detection, Evaluation, and Treatment of High Blood Cholesterol in Adults, JAMA, 285: 2486-2497, 2001; the contents of both of which are herein incorporated by reference in their entireties).

TABLE 5

Clinical Characterization and Analyte Means and Standard Deviations for Total Study Population

| Characteristic | Population; n = 767 Mean ± S.D. |
|---|---|
| Males (%) | 77.1 |
| Age (years) | 58.3 |
| Race (% white) | 78.5 |
| Prior MI (%) | 16.8 |
| Metabolic syndrome (%) | 35.6 |
| Statins (%) | 40.3 |
| Beta blockers (%) | 77.7 |
| Aspirin (%) | 81.9 |
| Ca channel blockers (%) | 19.8 |
| Nitrates (%) | 33.6 |
| ACE inhibitors (%) | 33.4 |
| Oral anticoagulants (%) | 17.9 |
| Glucose (mmol/L) | 5.01 ± 1.18 |
| Trig (mmol/L) | 2.24 ± 1.30 |
| ApoB (g/L) | 1.23 ± 0.28 |
| Cholesterol (mmol/L) | 5.11 ± 1.14 |
| ApoA1 (g/L) | 1.18 ± 0.25 |
| HDL (mmol/L) | 1.00 ± 0.28 |
| LDL-PPD (nm) | 26.3 ± 0.82 |
| Insulin (pmol/L) | 120 ± 168 |
| BMI (kg/m²) | 27.6 ± 4.9 |
| PAI-1 (μg/L) | 26.6 ± 24.7 |
| Lp(a) (mmol/L) | 0.63 ± 0.59 |

TABLE 5-continued

Clinical Characterization and Analyte Means and
Standard Deviations for Total Study Population

| Characteristic | Population; n = 767<br>Mean ± S.D. |
|---|---|
| CRP (mg/L) | 4.36 ± 6.87 |
| vWF (%) | 142 ± 62 |
| Fibrinogen (g/L) | 3.47 ± 0.82 |
| D-dim (µg/L) | 473 ± 415 |
| Factor VII (%) | 103 ± 43 |
| Factor VIIa (µg/L) | 2.52 ± 1.69 |

Figure 10:
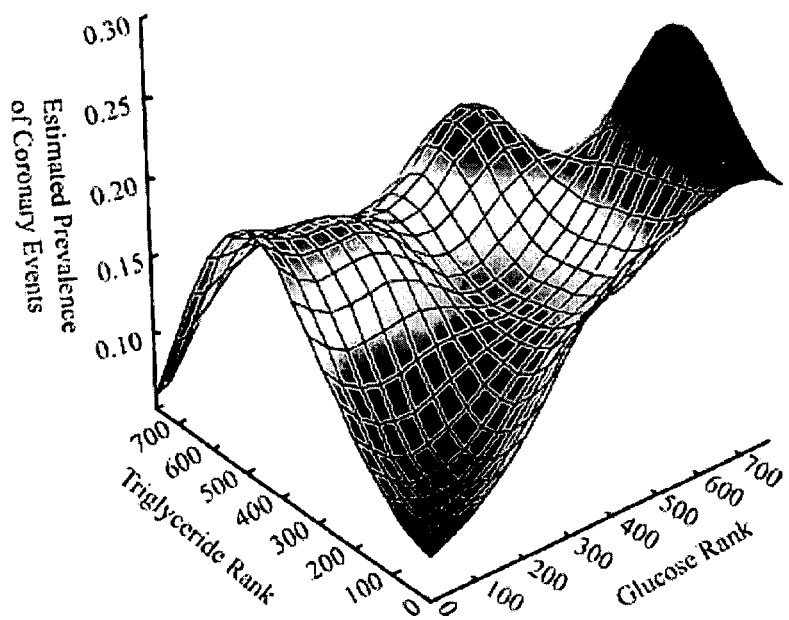
FIG. 10 is a surface map of estimated prevalence of recurrent coronary events as a function of glucose and triglyceride ranks in non-diabetic post-infarction patients.

FIG. 10 is a surface map of the estimated prevalence of coronary events as a function of glucose and triglyceride ranks for the study population. FIG. 11 is the corresponding contour map also showing individual patient points. The plots show three corresponding discrete peaks. To define these presumptively high-risk subgroups, patients were divided based on mean outcome event rate (15.9%) in the total population. Mean outcome event rate was chosen as cutoff point for determining high-risk subgroups as it is a standard, well-defined metric and conveniently results in division of the total population into roughly equal numbers of baseline and high-risk patients. In FIG. 11, the corresponding isoprevalence contour line at this value is superimposed on the plot. Regions with estimated prevalence higher than this value were defined to be high-risk regions. High-risk subgroups were separated from each other by tracing the valley floor between them. The three high-risk subgroups were designated as follows: Subgroup 1 (N=131), Subgroup 2 (N=112), Subgroup 3 (N=151), and a Baseline group (N=373) corresponding to remaining patients whose risk was determined to be less than the isoprevalence contour.

High-Risk Subgroup Validation

Figure 12:
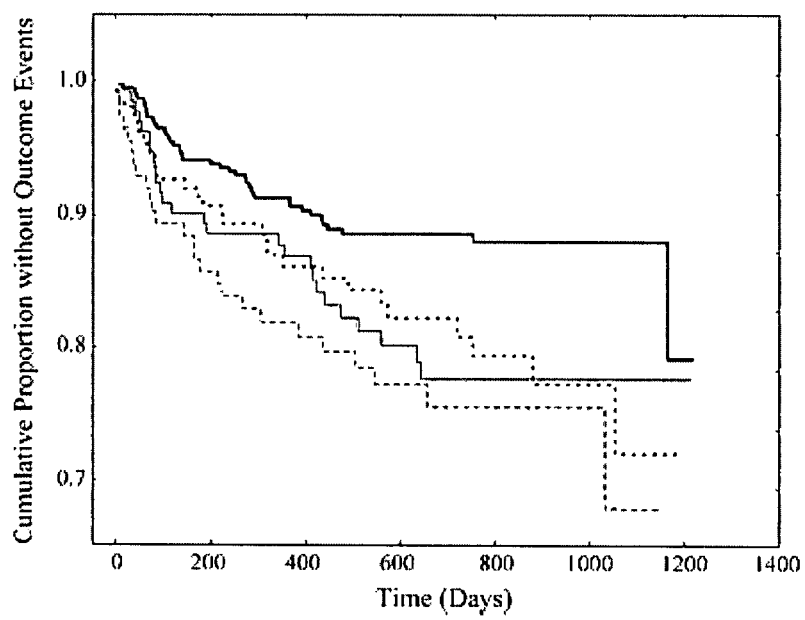
FIG. 12 is a presentation of Kaplan-Meier curves of baseline and three different high-risk patient subgroups.

To confirm high risk in the three subgroups, we first calculated outcome event rates in each of the high risk Subgroups as well as in the Baseline group. The rates were Subgroup 1—19.9%; Subgroup 2—23.2%; Subgroup 3—18.5%; and baseline—11.3%, respectively. This confirms higher risk in the three subgroups over and above baseline risk. Next, as shown in FIG. 12, we used Kaplan-Meier analysis to assess outcome events as a function of time for each of the three subgroups as compared to baseline. Log rank statistic p-values for these comparisons were 0.016, 0.001, and 0.024, respectively, demonstrating significantly worse outcome in the three high risk subgroups relative to baseline patients. Lastly, for each subgroup separately, univariate Cox analysis was run with time to outcome event as a function of binary independent variable with values corresponding to membership in the given subgroup (1) or baseline group (0). Odds ratios for each high-risk subgroup over baseline were all significant and along with 95 percentile confidence limits were 1.82 (1.12-2.97), 1.51 (1.18-1.93), and 1.20 (1.02-1.41), respectively. Results of corresponding analyses including adjustment for clinically significant variables (prior myocardial infarction, EF30, index infarct type by ECG) were similar although the case of subgroup 3 versus baseline did not achieve statistical significance p=0.128).

High-Risk Subgroup Characterization

Selected clinical characteristics along with means and standard deviations for 17 laboratory variables are given in Table 6 for baseline and high-risk subgroups. Also indicated are laboratory values in the high-risk subgroups that are significantly different from baseline (as determined by Mann-Whitney U-test).

TABLE 6

Clinical Characterization and Analyte Means and
Standard Deviations for Baseline and High-Risk Subgroups

| Characteristic | Baseline<br>N = 373<br>Mean ± S.D. | Subgroup 1<br>N = 131<br>Mean ± S.D. | Subgroup 2<br>N = 112<br>Mean ± S.D. | Subgroup 3<br>N = 151<br>Mean ± S.D. |
|---|---|---|---|---|
| Males (%) | 74.8 | 74.8 | 81.3 | 81.5 |
| Age (years) | 57.0 | 59.9 | 60.3 | 58.9 |
| Race (% White) | 79.4 | 84.7 | 83.0 | 67.6 |
| Prior MI (%) | 14.6 | 17.7 | 22.3 | 17.2 |
| Metabolic Syn (%) | 28.4 | 38.9 | 61.6 | 31.1 |
| Statins (%) | 46.6 | 36.6 | 33.9 | 32.5 |
| Beta blockers (%) | 79.4 | 78.6 | 78.6 | 72.2 |
| Aspirin (%) | 81.5 | 86.3 | 83.0 | 78.1 |
| Ca channel blockers (%) | 18.5 | 15.3 | 21.4 | 25.8 |
| Nitrates (%) | 33.0 | 29.0 | 42.0 | 33.1 |
| ACE inhibitors (%) | 34.3 | 29.0 | 34.8 | 33.8 |
| Oral anticoagulants (%) | 19.6 | 16.0 | 15.2 | 17.2 |
| Glucose (mmol/L) | 4.83 ± 1.22 | 4.21 ± 0.44* | 5.30 ± 0.34* | 5.92 ± 1.27* |
| Triglyceride (mmol/L) | 2.47 ± 1.68 | 2.32 ± 0.39* | 2.66 ± 0.44* | 1.32 ± 0.42* |
| ApoB (g/L) | 1.23 ± 0.28 | 1.26 ± 0.27 | 1.29 ± 0.27* | 1.16 ± 0.27* |
| Cholesterol (mmol/L) | 5.15 ± 1.22 | 5.23 ± 1.16 | 5.25 ± 1.01 | 4.80 ± 0.96* |
| ApoA1 (g/L) | 1.18 ± 0.26 | 1.21 ± 0.25 | 1.17 ± 0.20 | 1.17 ± 0.26 |
| HDL (mmol/L) | 1.02 ± 0.28 | 0.96 ± 0.26$^a$ | 0.90 ± 0.21* | 1.08 ± 0.31* |
| PPD (nm) | 26.2 ± 0.82 | 26.1 ± 0.74 | 25.8 ± 0.61* | 26.8 ± 0.74* |
| Insulin (pmol/L) | 115 ± 190 | 93 ± 82 | 147 ± 183* | 136 ± 153* |
| BMI (kg/m$^2$) | 27.3 ± 4.8 | 27.2 ± 5.0 | 28.2 ± 4.8* | 28.2 ± 5.0 |
| PAI-1 (µg/L) | 26.5 ± 26.7 | 23.4 ± 18.1 | 32.8 ± 25.8* | 25.1 ± 23.0 |
| Lp(a) (mmol/L) | 0.62 ± 0.57 | 0.65 ± 0.60 | 0.53 ± 0.59* | 0.70 ± 0.63 |
| CRP (mg/L) | 3.85 ± 5.12 | 4.96 ± 7.32 | 5.36 ± 10.61 | 4.33 ± 6.68 |
| VWF (%) | 144 ± 60 | 136 ± 62 | 142 ± 63 | 143 ± 65 |
| Fibrinogen (g/L) | 3.45 ± 0.78 | 3.46 ± 0.85 | 3.58 ± 0.98 | 3.45 ± 0.76 |
| D-dim (µg/L) | 474 ± 452 | 492 ± 408 | 479 ± 396 | 447 ± 334 |
| Factor VII (%) | 102 ± 44 | 108 ± 47 | 108 ± 41 | 96 ± 39 |
| Factor VIIa (µg/L) | 2.53 ± 1.75 | 2.52 ± 164 | 2.58 ± 1.63 | 2.46 ± 1.66 |

*Significantly different from baseline based on Mann-Whitney U-test($p < 0.05$).

For clinical characteristics, Table 6 demonstrates a lower percentage of whites in Subgroup 3, a higher percentage of patients with MS in Subgroup 2 (of the 38.4% of patients in this subgroup without MS, 79.1% of these met two of the criteria for MS), and similar values for all others. For laboratory value means relative to reference ranges, Subgroup 1 reveals elevated triglycerides (high; 2.26-5.63 mmol/L), cholesterol (borderline high; 5.17-6.18 mmol/L), and BMI (overweight; 25-25.9 kg/m$^2$), and decreased HDL (low; <1.03 mmol/L). Additionally, compared to baseline, Subgroup 1 has lower glucose, triglyceride and HDL. Subgroup 2 reveals relative to reference values elevated triglyceride (high; 2.26-5.63 mmol/L), cholesterol (borderline high; 5.17-6.18 mmol/L), and BMI (overweight; 25-25.9 kg/m$^2$), and decreased HDL (low; <1.03 mmol/L); and when compared to baseline, higher glucose, triglyceride, apoB, insulin, BMI, and PAI-1, and lower HDL, LDL peak particle diameter and Lp(a). Subgroup 3 reveals relative to reference values elevated BMI (overweight; 25-25.9 kg/m$^2$) and glucose (impaired fasting glucose; 5.6-6.9 mmol/L); and in comparison to baseline higher glucose, HDL, LDL peak particle diameter, and insulin, and lower triglyceride, apoB, and cholesterol. On this basis, subgroups were characterized as: Subgroup 1—normoglycermic, modestly hypertriglyceridemic; Subgroup 2—metabolic syndrome-enriched (MS-enriched); and Subgroup 3—prediabetic.

Significantly, the ability to detect and analyze in detail the attendant risk factors provides a powerful method for providing individualized treatment planning or prophylaxis for patients.

Risk Prediction within Individual Subgroups

The existence of high risk in the three subgroups relative to baseline patients prompted us to further examine risk by assessing whether any of the 17 laboratory parameters within each separate subgroup contributed to the risk observed. Separate Cox multivariate proportional hazards analysis was performed as a function of dichotomized laboratory parameters with adjustment for significant clinical variables for each of the three subgroups. A within-subgroup Cox analysis was not run for baseline in view of low risk and heterogeneity.

Table 7 provides significant clinical variables, significant laboratory variables in the univariate model, dichotomization cut points, and significant laboratory variables in the multivariate model along with odds ratios and 95th percentile confidence limits. All laboratory parameters significant in the univariate model resulted from dichotomization according to the highest risk quartile versus combined three lowest risk quartiles except for BMI, where only the combined two highest risk quartiles versus combined two lowest risk quartiles was successful. There were no significant medication effects.

The data in Table 7 reveal as significant and independent laboratory predictors of risk in the multivariate model the following: (1) BMI and fibrinogen in normoglycemic-modestly hypertriglyceridemic subgroup; (2) PAI-1 in MS-enriched subgroup; (3) glucose in pre-diabetic subgroup. For comparison, results of a traditional Cox analysis on the entire study population using the same dichotomization strategy revealed only apoB as a significant predictor of risk, a result consistent with previous studies not addressing risk heterogeneity.

TABLE 7

Separate Cox Proportional Hazards Model Analyses Of Within-Subgroup Risk For Each High-Risk Subgroup Giving N, Clinical Covariates Requiring Adjustment (P < 0.10), Significant Univariate Laboratory Variables (P < 0.05) Along With Dichotomization Cut Points, And Multivariate Results Of Simultaneous Entrance Of Significant Univariate Laboratory Variables With Adjustment For Relevant Clinical Covariates

| Population (N) | | Clinical covariates | Univariate model | Dichotomization cut points | Multivariate model |
|---|---|---|---|---|---|
| Subgroup (131) | 1 | Gender | BMI | 26.4 kg/m$^2$ | BMI 2.79 (1.17-6.63) |
| | | | Fibrinogen | 3.34 g/L | Fibrinogen 2.79 (1.29-6.04) |
| Subgroup (112) | 2 | None | PAI-1 | 45 µg/L | PAI-1 3.95 (1.81-8.61) |
| | | | D-dimer | 540 µg/L | |
| Subgroup (151) | 3 | Gender Claudication | Glucose Lp(a) | 6.05 mmol/L 0.98 mmol/L | Glucose 2.49 (1.17-5.33) |

Three high-risk subgroups in non-diabetic postinfarction patients were identified using a screening procedure based on ability to detect high-risk subgroups anywhere in bivariate risk-factor domains. By using this approach, within-subgroup laboratory markers of risk were identified as different in each subgroup. Serum glucose and triglyceride served as bivariate risk factor domains considering their importance in this population. Thus, subgroups were characterized based upon location in the glucose-triglyceride domain, as prediabetic, MS-enriched, and normoglycemic-modestly hypertriglyceridemic. High risk was anticipated in pre-diabetic and MS-enriched patients, but not in normoglycemic-modestly hypertriglyceridemic patients. Within-subgroup predictors of risk were as follows: glucose in pre-diabetic subgroup, PAI-1 in MS-enriched subgroup, and BMI and fibrinogen in normoglycermic-modestly hypertriglyceridemic subgroup. These findings underscore the notion that manifestation of risk, especially among emerging risk factors, may be a strong function of context deriving from presumably different pathophysiologic mechanisms underlying patient subgroup heterogeneity.

The pre-diabetic subgroup of this study was labeled as such given that most patients had fasting glucose levels over 5.55 mmol/L (100 mg/dL), the American Diabetes Association criterion for impaired fasting glucose, but less than 6.99 mmol/L (126 mg/dL), the criterion for diabetes. They also had fasting hyperinsulinemia, and on an average were overweight as well, although not all patients were overweight. A relatively small minority of these patients had glucose levels above 6.99 mmol/L (126 mg/dL), possibly due to existing but previously unrecognized diabetes.

Without wishing to be bound to any particular theory, cardiovascular disease and diabetes appears to stem from a commonality of environmental and genetic components, in essence growing from a "common soil" (Stern et al. Diabetes 44: 369-74. 1995; herein incorporated by reference in its entirety). Additionally, atherogenicity in the pre-diabetic state has been shown to be increased in pre-diabetic patients with insulin resistance in comparison to pre-diabetic patients with the type of insulin secretory deficits consistent with hyperinsulinemia seen in pre-diabetic patients of this study (Haffner et al., Circulation 101: 975-80, 2000; Festa et al. Circulation 108: 1822-30, 2003; herein incorporated by reference in their entirety).

It should be noted that identification of a known high-risk subgroup using our graphical approach verifies the utility of the method as disclosed herein. Embodiments of the presently disclosed method further showed glucose as a predictor of risk within the pre-diabetic subgroup. The role of hyperglycemia in cardiovascular disease in pre-diabetic and type two diabetic populations has been variable. Lack of association has been attributed to greater significance of postprandial hyperglycemia than fasting hyperglycemia and greater atherogenicity of the pre-diabetic state possibly overwhelming glycemic effects (Haffner, Am. J. Cardiol. 92 (Supp): 18J-26J, 2003, herein incorporated by reference in its entirety; Haffner et al., Circulation 101: 975-80, 2000).

The MS-enriched subgroup of this study was labeled on the basis that nearly two-third of patients met the criteria for MS and of the remaining third, nearly 80% met two of the criteria. Patients in this subgroup had the highest mean levels of triglyceride, apoB, insulin, BMI, and PAI-1, and lowest HDL and LDL peak particle diameter, all consistent with MS. This initially seemed discordant with the current results; however, in the previous study, the reference group of non-MS patients included patients from the other two high-risk subgroups of the present study. This is consistent with speculation that additional pathophysiologic mechanisms act in non-MS patients.

In the MS-enriched subgroup, PAI-1 levels were the highest of all subgroups, and the only one significantly different from total study population mean. In addition to PAI-1 elevations in the MS-enriched subgroup, PAI-1 was also the only blood marker to be an independent predictor of risk in the multivariate model within this subgroup with an odds ratio of nearly 4.

The remaining subgroup was labeled as normoglycemic-modestly hypertriglyceridemic. Additionally, these patients may also be overweight or obese and some patients had the lowest fasting insulin levels as compared to patients of other subgroups. As a result, the identification of this subgroup as high risk was unexpected. Many of these patients were overweight or obese but in a setting of relative normalcy in other blood markers including fasting insulin. Such a picture is consistent with obese patients demonstrating normal to high levels of insulin sensitivity variously termed "obese, metabolically normal" and "metabolically healthy, but obese" in whom low cardiovascular risk is presumed (Sims, Metabolism 50: 1499-504, 2001; Reaven, Ann. Intern. Med. 138: 420-3, 2003; Karelis et al., J. Clin. Endocrinol. Metab. 89: 2569-75, 2004; herein incorporated by reference in their entirety). High risk in this subgroup apparently arises from variables independent of insulin resistance, in contrast to patients of the MS-enriched subgroup where fasting insulin levels were not only elevated but were highest of the subgroups. This is consistent with a closer correlation of insulin and PAI-1 levels than of insulin and other inflammatory markers, such as fibrinogen.

The advantage of the present graphical approach to risk identification is illustrated by the unexpected finding of high risk in the normoglycemic-modestly hypertriglyceridemic subgroup. Traditional approaches would likely have missed the existence of this at-risk population. Additionally, not only is the present approach able to locate subgroups on the basis of unexpected relationships between factors, but it is able to better define subgroup boundaries. Thus, an additional advantage of the graphical screening approach is its potential utility in generating maps, not only of outcome prevalence, but any other binary variable as well. A general caveat in using the approach is that there should preferably be as even a distribution of points over the bivariate risk domain as possible to minimize generation of spurious peaks and valleys that could result from large clusters and/or gaps in data. Transformation of independent variable values to rankings appears to be a reasonable approach.

EXAMPLE 4

Relationship Between Glycoprotein Ibα Variants, Diabetes and Risk of Coronary Events Study Population The study population comprised patients of the THROMBO prospective postinfarction study. There were a total of 1,045 non-diabetic and diabetic patients, of which 940 had complete biomarker results and 903 were genotyped with respect to the Gp-Ibα T145M polymorphism. For the diabetic study group, there were a total of 199 patients, with 173 having complete serum biomarker levels, and 145 having complete biomarker levels as well as T145M polymorphism genotyping. Reference populations comprised non-diabetic patients of the THROMBO study. Recurrent coronary outcome events for this study were cardiac death, myocardial infarction (MI), or unstable angina (hospitalization during follow-up with an increase in either frequency or duration of angina symptoms or with development of new angina at rest with both requiring ischemic ECG changes without enzyme elevation), whichever occurred first. Average patient follow-up was 26 months. Diabetes mellitus was identified as use of oral hypoglycemic agents or insulin.

Blood Markers

Two months after index MI, blood markers were determined on fasting sera. Levels of the following 17 markers were determined as discussed in previous examples, including apoB, total cholesterol, apoA1, HDL cholesterol (HDL), triglyceride, LDL peak particle diameter, glucose, insulin, plasminogen activator inhibitor-1 (PAI-1), lipoprotein(a) (Lp (a)), C-reactive protein (CRP), von Willebrand factor antigen, fibrinogen, D-dimer, Factor VII, Factor VIIa, and lipoprotein-associated phospholipase $A_2$ (Lp-PLA$_2$). LDL peak particle diameter was determined by gradient gel electrophoresis by previously published methods (Rainwater et al., J. Lip. Res. 38: 1261-1266, 1997; Rainwater, Meth. Mol. Biol. 110: 137-151; both of which are herein incorporated by reference in their entireties). A commercial colorimetric assay (Cayman Chemical Co., Ann Arbor, Mich.) was used to determine plasma Lp-PLA$_2$ activity as described previously (Corsetti et al., Clin. Chem. 252: 1331-1338, 2006; herein incorporated by reference in its entirety) using 2-thio-PAF as substrate and according to manufacturer's directions; 5,5'-dithio-bis-(2-nitrobenzoic acid) was used to detect enzymatic hydrolysis of the acetyl thioester bond with monitoring at 405 nm. Two control products were run with each assay. Between-assay coefficients of variation were 1.6% for a low control and 5.6% for a control near the sample mean. All but two samples gave rates greater than the low control. Samples were run in duplicate and the average coefficient of variation was 2.5%. Enzyme activity was expressed in units of µmol/min/mL.

Genotyping the Gp-Ibα T145M Polymorphism

Blood samples were collected at study enrollment. Buffy coats were isolated and stored at −70° C. until extracted for DNA analysis. Genotyping was performed under contractual agreement with Millennium Pharmaceuticals (Cambridge, Mass.) using the TaqMan method with differentially labeled probes complementary to either a specific T or C nucleotide within the Gp-Ibα coding sequence (ref SNP ID: rs6065). A C to T substitution at position 1018 of the coding sequence in the Gp-Ibα gene changes Thr to Met at position 145 (Wenger et al., Biochem. Biophys. Res. Commun. 156: 389, 1988; Murata et al., Blood 79: 3086-3090, 1992; DiPaola et al., J. Thrombos. Haemostas. 3: 1511-1521, 2005; Douglas et al., Heart 87: 70-74, 2002; all of which are herein incorporated by reference in their entireties). When a T nucleotide is present the gene encodes for Met, while when a C nucleotide is present, Thr is encoded at the position.

Each individual was classed according to genotype, with those homozygous for the T nucleotide variant being termed MM (representing Met at position 145 in both alleles), and those homozygous for the or C nucleotide variant being termed TT (representing Thr at position 145 for both alleles). Heterozygous individuals were termed TM. Genotype frequencies in the study subjects were consistent with population diversity data reported in the NCBI Reference SNP database (TT-76.4%, TM-20.5%, and MM-0.3%).

Statistical Analyses

Study design involved post-hoc analyses of the prospective THROMBO study. All analyses were performed with Statistica 7.0 (StatSoft, Inc., Tulsa, Okla.). Variables were adjusted for age using linear regression. The Mann-Whitney U test was used to detect significant differences between groups. The Chi-square test was used to detect significant differences in proportions and polymorphism distributions. Significance level for all testing was at the $p<0.05$ level unless otherwise stated.

Significant variables associated with time to outcome event were determined using Kaplan-Meier analysis (log rank statistic, $p<0.05$) and Cox multivariable proportional hazards regression modeling. To assess risk of secondary coronary events as a function of blood marker variables, Cox regression was applied using the previously noted 17 laboratory markers as independent variables. Each marker was treated as a dichotomized independent variable in separate univariate models. In order to determine optimal cut-points for dichotomization of marker levels, two dichotomization schemes were applied to each variable. These were with cut-points at the seventy-fifth and fiftieth percentile levels for all blood markers except for apoA1 and HDL, which were at the fiftieth and twenty-fifth percentile levels, in accordance with inverse association of marker level with risk for these two parameters. For markers with univariate results significant in both dichotomization schemes, the best-fit result was used in subsequent analyses. The T145M polymorphism was treated as a binary independent variable (0 for TT; 1 for TM or MM).

The following clinical covariates were evaluated in separate univariate models: sex, race, smoking, prior MI (an MI sometime in the past before the MI of study enrollment), myocardial index which is index infarct type by ECG (Q-wave versus non Q-wave), pulmonary congestion, ejection fraction during entrance MI-EF30 (>0.30, ≤0.30), and claudication. Multivariable modeling with adjustment for resulting significant clinical covariates ($p<0.1$) was performed with simultaneous entry of the T145M polymorphism and all univariate significant ($p<0.05$) dichotomized blood markers as independent variables. Assessment of medication effects was performed by single entry into the resulting multivariable models of the following medications: statins, beta blockers, aspirin, calcium channel blockers, nitrates, ACE-inhibitors, and oral anticoagulants, ($p<0.05$). Joint risk for combinations of risk factors was analyzed by Kaplan-Meier analysis and evaluation of relative outcome event rates (compared to patients with no risk factors) for risk factor combinations.

Clinical and laboratory characteristics of the diabetic study population (N=173) are given in Table 8. In comparison to non-diabetic patients (N=767) of the THROMBO study, the diabetic group had significantly higher proportions of female (32.9% versus 22.9%), and black patients (38.2% versus 21.5%) as well as significantly higher proportions of patients with recurrent coronary outcome events (29.5% versus 15.9%), prior MI (an MI sometime in the past before the MI of study enrollment, 24.3% versus 16.8%), on nitrates (45.1% versus 33.6%), and on ACE inhibitors (50.9% versus 33.4%). In terms of means and standard deviations, diabetic patients in comparison to non-diabetic patients had a significantly higher value of BMI (29.2±5.4 kg/m$^2$ vs. 27.6±4.9 kg/m$^2$) and significantly higher levels of glucose (8.69±3.91 mmol/L vs. 5.01±1.18 mmol/L), insulin (211±272 pmol/L vs. 120±168 pmol/L), PAI-1 (35.0±36.3 µg/L vs. 26.6±24.7 µu/L), CRP (7.42±10.55 mg/L vs. 4.36±6.87 mg/L), VWF (175%±74% vs. 142%±62%), fibrinogen (3.74±1.01 g/L vs. 3.47±0.82 g/L), and D-dimer (569±485 µg/L vs. 473±415 µg/L). None of the lipoprotein-related traits, including levels of Lp-PLA$_2$, were significantly different between diabetic and non-diabetic patients.

TABLE 8

Clinical Characterization and Blood Marker Means and Standard Deviations for Patients With Diabetes

| Characteristic | Patients with Diabetes |
|---|---|
| Recurrence Rate (%) | 29.5 |
| Males (%) | 67.1 |
| Race (% White) | 61.8 |
| Prior MI (%) | 24.3 |
| Statins (%) | 34.1 |
| Beta Blockers (%) | 71.1 |
| Aspirin (%) | 79.2 |
| Calcium Channel Blockers | 22.5 |
| Nitrates (%) | 45.1 |
| ACE Inhibitors (%) | 50.9 |
| Oral Anticoagulants (%) | 17.3 |

| | Mean ± S.D. |
|---|---|
| Age (Years) | 60.3 ± 11.4 |
| BMI (kg/m$^2$) | 29.2 ± 5.4 |
| Blood Markers | |
| ApoB (g/L) | 1.24 ± 0.29 |
| Cholesterol (mmol/L) | 5.11 ± 1.11 |
| ApoA1 (g/L) | 1.19 ± 0.26 |
| HDL (mmol/L) | 1.03 ± 0.34 |
| Triglyceride (mmol/L) | 2.36 ± 1.39 |
| LDL peak diameter (nm) | 26.16 ± 0.79 |
| Glucose (mmol/L) | 8.69 ± 3.91 |
| Insulin (pmol/L) | 211 ± 272 |
| PAI-1 (µg/L) | 35.0 ± 36.3 |
| Lp(a) (mmol/L) | 0.62 ± 0.61 |
| CRP (mg/L) | 7.42 ± 10.55 |
| Von Willebrand Factor (%) | 175 ± 74 |
| Fibrinogen (g/L) | 3.74 ± 1.01 |

TABLE 8-continued

Clinical Characterization and Blood Marker Means and Standard Deviations for Patients With Diabetes

| | |
|---|---|
| D-dimer (µg/L) | 569 ± 485 |
| Factor VII (%) | 106 ± 47 |
| Factor VIIa (ng/mL) | 2.61 ± 1.77 |
| Lp-PLA$_2$ (µmol/min/mL) | 25.43 ± 5.44 |

The Gp-Ibα Polymorphism (T145M)

Genotype frequencies in the study population (N=145; TT-80.7%, TM-17.9%, and MM-1.4%) were in Hardy-Weinberg equilibrium. Distribution of frequencies as a function of race (whites; TT-81.6%, TM-17.4%, and MM-1.0% and blacks; TT-78.7%, TM-19.2%, and MM-2.1%) were not different from each other (p=0.83). For subsequent analyses, the polymorphism was dichotomized as TM plus MM versus TT. Based on this dichotomization, there were no significant differences as a function of variant in the clinical markers of Table 8 except for gender (TM plus MM; 10.0% in females, 24.2% in males, p=0.041); and no differences in the proportions of patients on medication. Additionally, as shown in Table 9, there were no significant differences in blood marker levels as a function of the dichotomized polymorphism, and there was no difference in variant distribution between diabetic and non-diabetic patients (N=663).

TABLE 9

Blood Marker Means and Standard Deviations for Diabetic Patients as a Function of T145M Polymorphism in the Gp-Ibα Subunit

| Blood Marker | TT | TM plus MM |
|---|---|---|
| ApoB (g/L) | 1.22 ± 0.28 | 1.27 ± 0.26 |
| Cholesterol (mmol/L) | 5.09 ± 1.09 | 4.9 ± 0.83 |
| ApoA1 (g/L) | 1.21 ± 0.28 | 1.12 ± 0.19 |
| HDL (mmol/L) | 1.07 ± 0.38 | 0.99 ± 0.26 |
| Triglyceride (mmol/L) | 2.44 ± 1.36 | 1.96 ± 0.67 |
| LDL peak diameter (nm) | 26.14 ± 0.84 | 26.11 ± 0.57 |
| Glucose (mmol/L) | 8.54 ± 3.72 | 8.97 ± 4.09 |
| Insulin (pmol/L) | 188 ± 176 | 220 ± 268 |
| PAI-1 (µg/L) | 35.1 ± 29.8 | 32.2 ± 30.8 |
| Lp(a) (mmol/L) | 0.58 ± 0.57 | 0.71 ± 0.71 |
| CRP (mg/L) | 7.86 ± 11.53 | 7.32 ± 9.82 |
| Von Willebrand Factor (%) | 180 ± 75 | 163 ± 59 |
| Fibrinogen (g/L) | 3.79 ± 1.06 | 3.65 ± 0.89 |
| D-dimer (µg/L) | 562 ± 483 | 503 ± 342 |
| Factor VII (%) | 104 ± 49 | 101 ± 39 |
| Factor VIIa (ng/mL) | 2.69 ± 1.84 | 2.53 ± 1.88 |
| Lp-PLA$_2$ (µmol/min/mL) | 25.84 ± 5.56 | 25.11 ± 4.76 |

Gp-Ibα Polymorphism (T145M) and Risk of Recurrent Coronary Events

Figure 13:
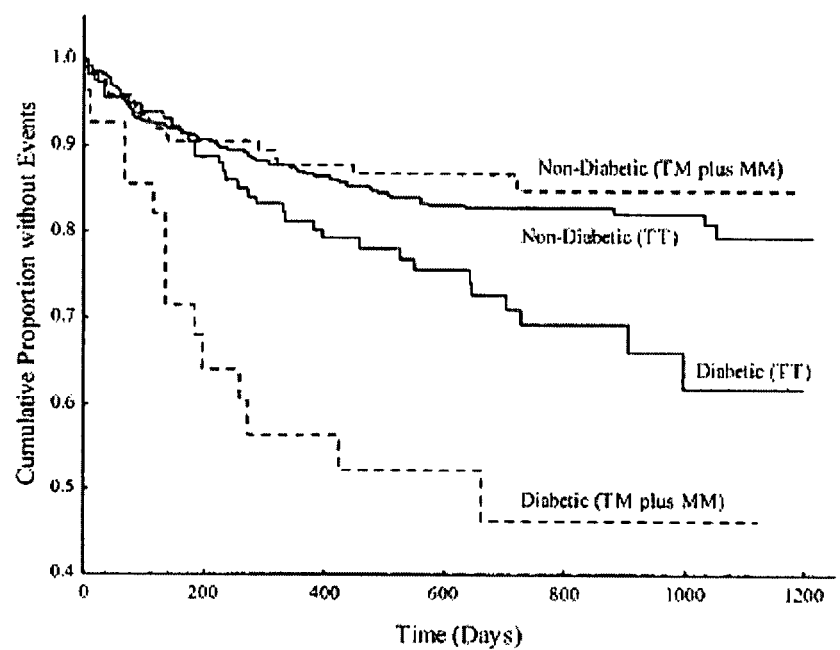
FIG. 13 is a graph of Kaplan-Meier curves of the proportion of patients without recurrent coronary events as a function of Gp-Ibα variant (solid lines—TT; dashed lines—TM plus MM) for diabetic patients (log rank p=0.013) and for non-diabetic patients (log rank p=0.49).

Diabetic postinfarction patients with the M allele demonstrated a coronary event recurrence rate of 50%, vs. 27.4% (p=0.02) for patients homozygous having the T allele. There was no statistically significant difference in the corresponding rates for non-diabetic patients (16.4% vs. 13.7%, p=0.45). To confirm that the effect of the T145M polymorphism on outcome events was specific to diabetic patients, interaction between diabetes and the T145M polymorphism was tested in the Cox regression for the combined non-diabetic and diabetic patients groups. Results demonstrated the interaction term to be statistical significance (p=0.013) underscoring the specific effect of the polymorphism on diabetic patients. The effect of the polymorphism is illustrated in FIG. 13 by Kaplan-Meier curves showing the proportion of diabetic postinfarction patients without recurrent coronary events as a function of dichotomized T145M polymorphism. The results reveal a significantly poorer outcome for patients with the M allele (p=0.013) as compared to non-diabetic postinfarction patients who demonstrated no difference (p=0.49). Thus, while diabetic patients are already in a high risk category for recurrent coronary events, the risk of an event is significantly affected by their Gp-Ibα genotype.

Multivariable Risk as a Function of Gp-Ibα Polymorphism (T145M) and Blood Markers Table 10 provides results for significant predictors of recurrent coronary outcome events from univariate Cox proportional hazards regression of the T145M polymorphism, clinical covariates (p<0.1), and the 17 blood markers of Table 8 dichotomized as described above (seventy-fifth percentile for glucose; fiftieth percentile for HDL, triglyceride, factor VIIa, and Lp-PLA$_2$; variables with significant associations with recurrent coronary outcome were only significant in one of the two dichotomization schemes). Results of multivariate modeling using simultaneous entry of all variables of Table 10 demonstrated continued significance of all variables except glucose and Factor VIIa. Further, to test medication effects on the model, multivariable models using all the variables of Table 10 except glucose and Factor VIIa were performed with single entry of each of the seven medications of Table 8. Only calcium channel blockers were found to be significant in this series of models. Further, HDL lost significance in this model. Thus, the final multivariable model adjusted for significant clinical covariates (prior MI and claudication) and medication effects (calcium channel blockers) revealed as significant: T145M polymorphism of Gp-Ibα, triglyceride, and Lp-PLA$_2$. Hazard ratios, 95% CI's, and p values are given in Table 11 along with Kaplan-Meier curves for triglyceride and Lp-PLA$_2$ in FIG. 14, panel A and panel B, respectively.

TABLE 10

Significant Variable of Gp-Iba Polymorphism (T145M), Blood Markers, and Clinical Co-variates as Predictors of Recurrent Coronary Outcome Events

| Variable | Dichotomization Cut-Point | Hazard Ratio (95% CI) | P Value |
|---|---|---|---|
| T145M | TT/TM plus MM | 2.31 (1.23-4.33) | 0.009 |
| Glucose | 10.55 mmol/L (190 mg/dL) | 1.99 (1.13-3.52) | 0.017 |
| HDL | 0.98 mmol/L (38 mg/dL) | 0.52 (0.30-0.93) | 0.026 |
| Triglyceride | 2.07 mmol/L (183 mg/dL) | 2.03 (1.14-3.64) | 0.017 |
| Factor VIIa | 2.22 ng/mL | 0.54 (0.31-0.97) | 0.038 |
| Lp-PLA$_2$ | 24.92 µmol/min/mL | 1.86 (1.05-3.31) | 0.034 |
| Prior MI | No/Yes | 2.23 (1.26-3.94) | 0.006 |
| Claudication | No/Yes | 2.57 (1.39-4.76) | 0.003 |

TABLE 11

Results of Cox Multivariate Modeling Adjusted for Significant Clinical Covariates and Medication Effects in Diabetic Post-infarction Patients

| Variable | Dichotomization Cut-Point | Hazard Ratio (95% CI) | P Value |
|---|---|---|---|
| T145M | TT/TM plus MM | 3.73 (1.90-7.33) | <0.001 |
| Triglyceride | 2.07 mmol/L (183 mg/dL) | 2.91 (1.52-5.56) | 0.017 |
| Lp-PLA$_2$ | 24.92 µmol/min/mL | 2.78 (1.45-5.35) | 0.002 |
| Prior MI | No/Yes | 1.73 (0.91-3.28) | 0.095 |
| Claudication | No/Yes | 2.25 (1.12-4.52) | 0.023 |
| Ca Channel Blockers | No/Yes | 2.68 (1.39-5.18) | 0.003 |

A series of additional analyses were performed to address several issues. First, to rule out potentially confounding effects on results of the gender difference in the proportion of patients with the M allele as noted above (10.0% in females, 24.2% in males), the complete model was adjusted for gender and re-run. Results were essentially unchanged. Lack of a gender effect was also supported by similar ratios of secondary recurrent event rates for patients the M allele as compared to patients homozygous for the T allele (females-2.08; males-1.81) as well as similar values for hazard ratios in gender-specific Cox analyses of patients with the M allele vs. patients homozygous for the T allele, adjusted for significant clinical covariates (females-3.25, p=0.16; males-2.91, p=0.008). Close approach but failure to reach statistical significance in females was likely due to low patient numbers.

Effects of race on results were also assessed. As noted above, the distribution of the T145M polymorphism did not vary as a function of race. This was consistent with results of multivariable analyses with race forced into the model (either alone or with gender forced in as well). Third, to assess effects of inclusion of all diabetic patients regarding the T145M polymorphism, univariate Cox analysis was performed using mean substitution for the value of the T145M variable for diabetic patients without genotyping. Results for the total population of diabetic patients (N=199) were essentially unchanged.

No significant two-factor interactions were found among the three significant marker variables (T145M polymorphism, triglycerides, and Lp-PLA$_2$). To explore joint risk associated with combinations of the three risk markers, Kaplan-Meier curves, shown in FIG. 15, were generated for patients having zero, one, two, or three risk markers. Log rank p values for comparison of curves relative to patients with no risk markers were: one risk marker, p=0.15; two risk markers, p=0.018; and three risk markers, p<0.00001. Recurrent coronary event rates as a function of number of risk markers and p-values relative to patients with zero higher risk markers were: zero markers, 10.7%; one marker, 26.2% (p=0.099); two markers. 43.2% (p=0.005); and three markers, 87.5% (p=0.0002). Thus, relative outcome rates (compared to patients with no risk factors) for risk factor combinations of one, two, or three risk factors were 2.4, 4.0, and 8.2, respectively. This represents an approximately multiplicative relationship between recurrent risk and increasing numbers of risk factors.

Results of the current work on diabetic patients of the THROMBO prospective postinfarction study, using multivariable modeling adjusted for clinical risk factors, demonstrated significant and independent association with risk of recurrent coronary events for the M allele of the T145M polymorphism of the platelet GP-Ibα subunit, hypertriglyceridemia, and elevated Lp-PLA$_2$. Additionally, joint risk increased approximately multiplicatively with number of risk factors. In contrast, for non-diabetic postinfarction patients, the T145M polymorphism was not a predictor of risk nor was hypertriglyceridemia.

Results of population studies assessing the T145M polymorphism and atherosclerosis-related disease risk have been mixed. Multiple population studies failed to show differences in T145M variant frequencies between cases and controls (Hato et al., Am. J. Cardiol. 80: 1222-1224, 1997; Sperr et al., Thromb. Res. 90: 117-123, 1998; Ito et al., Int. J. Hematol. 70: 47-51, 1999; Ardissino et al., Blood 94: 46-51, 1999; Ishida et al., Br. J. Haematol. 111: 1247-1249, 2000; Ozelo et al., Thromb. Haemost. 92: 384-386, 2004; herein incorporated by reference in their entirety) including one in diabetic patients (Sperr et al., Thromb. Res. 90: 117-123, 1998; herein incorporated by reference in its entirety). However, other studies have shown associations of the polymorphism and CAD, all with M allele-associated risk (24-27). These include associations of the M allele with: severity of CAD in MI and angina patients less than 60 years old (Murata et al., Circulation 96: 3281-3286, 1997; herein incorporated by reference in its entirety); incidence of MI or unstable angina in postinfarction patients (Gonzalez-Conejero, et al., Blood 92: 2771-2776, 1998; herein incorporated by reference in its entirety); coronary thrombosis, fatal MI, and sudden cardiac death for early middle-aged patients (Mikkelsson et al., Circulation 104: 876-880, 2001; herein incorporated by reference in its entirety); and postoperative myocardial ischemia in vascular surgery patients (Faraday et al., Anaesthesiol. 101: 1291-1297, 2004; herein incorporated by reference in its entirety). For cerebrovascular disease (CVD), one study demonstrated no association (Carlsson et al., Stroke 28: 1392-1395, 1997; herein incorporated by reference in its entirety); while others demonstrated associations of the M allele with various aspects of CVD (Mikkelsson et al., Circulation 104: 876-880, 2001; Sonoda et al., Stroke 31: 493-497, 2000; Sonoda et al., Thromb. Haemost. 85: 573-574, 2001; herein incorporated by reference in their entirety). Results of the current work are in agreement with most studies described above in demonstrating M allele-associated risk. However, our finding of M allele-associated risk only in diabetic postinfarction patients is a new finding that was likely facilitated by performing separate studies in non-diabetic and diabetic patient groups.

As in population studies, results of platelet function studies for T145M variants are mixed. No differences for variants were reported for: ADP-induced platelet aggregation and VWF binding (Mazzucato et al., Transfusion 36: 891-894, 1996; herein incorporated by reference in its entirety); VWF binding to truncated GP-Ibα T and M variant proteins (Li et al., Blood 95: 205-211, 2000; herein incorporated by reference in its entirety); and collagen-epinephrine closure time (Jilma-Stohlawetz et al., Br. J. Haematol. 120: 652-655, 2003; herein incorporated by reference in its entirety). However, other studies do report differences including: greater inhibition of VWF-mediated platelet agglutination by aurintricarboxylic acid, a VWF antagonist, for M allele carriers but no difference in prolongation of collagen-ADP closure time (Boncler et al., J. Mol. Med. 80: 796-801, 2002; herein incorporated by reference in its entirety); increased ristocetin-induced and shear-stress induced agglutination and shortened collagen-epinephrine closure time for homozygous T subjects (Yee et al., Blood 102: 783a, 2003; herein incorporated by reference in its entirety); greater binding of VWF to T variant N-terminal fragments of GP-Ibα transfected Chinese hamster ovary (CHO) cells (Ulrichts et al., Ateriscler. Thromb. Vasc. Biol. 23: 1302-1307, 2003; herein incorporated by reference in its entirety); mildly shortened collagen-ADP closure time for CAD patients homozygous for T (Porto et al., Blood Coagul. Fibrinolys. 16: 97-104, 2005; herein incorporated by reference in its entirety); and in CHO cell transfectants of T145M and a second GP-Ibα polymorphism (VNTR; variable number tandem repeats) variants, stronger interaction of VWF with M variant of T145M (Matsubara et al., Br. J. Haematol. 128: 533-539, 2005; herein incorporated by reference in its entirety). Thus, there is ample evidence demonstrating functional differences in T145M variants.

Results of the current study show a striking difference between diabetic and non-diabetic patients regarding M allele-associated risk. Without wishing to be held to a particular hypothesis, we believe that endothelial dysfunction is a significant process underlying this difference. This notion is supported by a recent report of greater association in diabetic patients of endothelial dysfunction with cardiovascular mortality than in non-diabetic patients (de Jager et al., Arterioscler. Thromb. Vasc. Biol. 26: 1086-1093, 2006; herein incorporated by reference in its entirety). Indeed, endothelial dysfunction is more pronounced in diabetic patients of the current study as demonstrated by higher levels of two common serum markers of endothelial dysfunction (vWF and PAI-1). Thus, in diabetic patients, it may be that greater levels of endothelial dysfunction accentuate effects of functional differences between T145M variants through increased platelet binding to endothelium resulting from the endothelial damage and high vWF levels associated with endothelial dysfunction.

In addition to T145M, results of the present study for diabetic patients show significant and independent risk associated with hypertriglyceridemia and elevated Lp-PLA$_2$. Hypertriglyceridemia is a well-known feature of diabetic dyslipidemia and associated risk (Kraus, Diabetes Care 27: 1496-1504, 2004; herein incorporated by reference in its entirety). Lp-PLA$_2$, an emerging biomarker of atherosclerotic disease, is a circulating enzyme that hydrolyzes altered phospholipids of oxidized lipoprotein particles to generate atherogenic species (Caslake et al., Curr. Opin. Lipidol. 14: 347-352, 2003; Tselepsis et al., Atherscler. Supp. 3: 57-68, 2002; herein incorporated by reference in their entirety). It has special affinity for highly oxidized, small-dense LDL particles characteristic of diabetic dyslipidemia (Gazi et al., Clin. Chem. 51: 2264-2273, 2005; herein incorporated by reference in its entirety). Risk factor interactions are likely responsible for the extremely poor outcome in diabetic patients having all three risk factors. Thus, hypertriglyceridemia may drive formation of easily oxidizable, small dense LDL particles with subsequent hydrolysis by Lp-PLA$_2$ to generate pro-inflammatory species highly injurious to vascular endothelium resulting in intensified endothelial dysfunction.

The present example did not include a GP-Ibα haplotype analysis. While haplotpye analysis is often useful in narrowing the localization of the functional genetic variant, the validity of our study conclusions linking genetic variation in GP-Ibα to coronary risk stands, and in fact, the T145M SNP is a coding variant known to demonstrate functional differences in GP-Ibα subunit action (Murata et al., Blood 79: 3086-3090, 1992; herein incorporated by reference in its entirety).

In conclusion, the disclosed method is effective to identify groups having significantly increased risk of recurrent coronary events based on combinations of risk factors. In particular, the presence of the M allele of the platelet GP-Ibα subunit polymorphism (T145M), along with hypertriglyceridemia and elevated Lp-PLA$_2$, predicts risk for recurrent coronary events in diabetic postinfarction patients. In contrast, for non-diabetic postinfarction patients, only elevated Lp-PLA$_2$ predicts risk. These findings underscore differences in pathophysiologic mechanisms associated with cardiovascular disease in diabetic patients and support an important role for endothelial dysfunction in diabetes.

More generally, in embodiments of the present disclosure it is possible to determine a relative risk, or probability of occurrence of an event, using data representative of risk-factor parameters that are either continuous in nature (e.g. circulating levels of a risk factor parameter) or discrete (e.g., the occurrence or non-occurrence of an event; the presence or absence of a genetic polymorphism, and the like), or combinations of continuous or discrete data. Discrete data can further comprise a binary value, or the presence or absence of a particular factor, for example a risk factor or pre-existing condition, or history of a condition.

For example, variables can include, without limitation, such things as blood levels of apoA1, apoB, total serum cholesterol, HDL, cholesterol, triglyceride, glucose, insulin, plasminogen activator inhibitor-1, lipoprotein (a), C-reactive protein, von Willibrand factor, von Willibrand factor antigen, fibrinogen, D-dimer, Factor VII, Factor VIIa, and lipoprotein-associated phospholipase A$_2$, or physical characteristics such as an LDL peak particle diameter can comprise risk-factor parameters. Likewise, discrete variables can include, without limitation, such factors as a history of type II diabetes, a history of a pre-diabetic syndrome, a history of metabolic syndrome, a polymorphism in NAD(P)H oxidase, a polymorphism in Glycoprotein-Ibα, other genetic polymorphisms, a history of obesity, a body mass index, and a history of a previous coronary event. All are useable as risk-factor parameters in context with the methods of the present disclosure.

The skilled artisan will recognize the interchangeability of various features from different embodiments. Similarly, the various features and steps discussed above, as well as other known equivalents for each such feature or step, can be mixed and matched by one of ordinary skill in this art to perform compositions or methods in accordance with principles described herein. Although the disclosure has been provided in the context of certain embodiments and examples, it will be understood by those skilled in the art that the disclosure extends beyond the specifically described embodiments to other alternative embodiments and/or uses and obvious modifications and equivalents thereof. Accordingly, the disclosure is not intended to be limited by the specific disclosures of embodiments herein.

What is claimed is:

1. A method for identifying risk of a coronary event based on an analysis of multiple risk factors, comprising:
   providing a reference database comprising a plurality of reference data points, each reference data point representing an (n+1)-dimensional vector comprising a value for each of n risk-factor parameters, wherein n≥2;
      wherein the n risk-factor parameters comprise an HDL level and a C-reactive protein (CRP) level;
      wherein each reference data point further comprises a corresponding outcome value; and
      wherein the outcome value is determined by the prior occurrence or non-occurrence of a coronary event;
   mapping each reference data point as a map point in a (n+1)-dimensional space, thereby producing a reference map;
      wherein the position of each map point in n dimensions is determined by the values of the associated reference data point's n risk-factor parameters; and
      wherein the position of each map point in the (n+1)th dimension is determined by the outcome value in the associated reference data point;
   applying, using a processor, an interpolation algorithm to the reference map to produce an interpolated (n+1)-dimensional map;
      wherein the interpolated (n+1)-dimensional map comprises a surface that defines a function, the function mapping values of the n risk-factor parameters to predicted outcome values; and
      wherein each of the predicted outcome values, as determined by the HDL level and the CRP level, represents a relative risk and/or a probability of occurrence of the coronary event;
   mapping a query data point associated with a person, comprising values for each of the n risk-factor parameters, onto the interpolated (n+1)-dimensional map;

wherein the location of the query data point on the interpolated (n+1)-dimensional map is determined, at least in part, by the query data point's values of the n risk-factor parameters;

determining an indicator based on one of the predicted outcome values associated with the query data point by mapping, with the function, the query data point's values to a point in the surface, the point in the surface being indicative of the one of the predicted outcome values; and outputting, to an output device, the indicator; wherein the indicator indicates that when the person's HDL level is greater than 1 mmol/L, and given the person's CRP level, (a) an HDL level greater than the person's HDL level presents an increased risk of a coronary event; or (b) an HDL level lower than the person's HDL level presents a decreased risk of a coronary event.

2. The method of claim 1, wherein n=2.

3. The method of claim 1, wherein at least one of the risk-factor parameters comprises a continuous range of values.

4. The method of claim 1, wherein at least one of the risk-factor parameters comprises a range of discrete values.

5. The method of claim 1, wherein at least one of the risk-factor parameters comprises a binary range of values.

6. The method of claim 1, wherein at least one of the risk-factor parameters comprises a presence or absence of a risk factor, a pre-existing condition, or a history of a pre-existing condition.

7. The method of claim 1, wherein the coronary event comprises a malignant arrhythmia, a myocardial infarction, and/or an episode of unstable angina.

8. The method of claim 1, wherein the relative risk associated with the query data point comprises a range of values of relative risk.

9. The method of claim 1, wherein the probability associated with the query data point comprises a range of values of probability.

10. The method of claim 1, wherein the surface comprises points representing values or functions of probabilities of occurrence of the coronary event.

11. The method of claim 1, further comprising outputting a graphical representation of the interpolated (n+1)-dimensional map to an output device.

12. The method of claim 1, wherein the output device comprises a numerical display, a graphical display, an electronic monitor, paper, an LCD, and/or a hand-held display.

13. The method of claim 1, wherein at least one of the n risk-factor parameters is selected from the group consisting of blood levels of apoA1, apoB, total serum cholesterol, cholesterol, triglyceride, glucose, insulin, plasminogen activator inhibitor-1, lipoprotein (a), C-reactive protein, von Willibrand factor, von Willibrand factor antigen, fibrinogen, D-dimer, Factor VII, Factor VIIa, and lipoprotein-associated phospholipase $A_2$.

14. The method of claim 1, wherein at least one of the n risk-factor parameters is selected from the group consisting of an LDL peak particle diameter, a history of type II diabetes, a history of a pre-diabetic syndrome, a history of metabolic syndrome, a polymorphism in NAD(P)H oxidase, a polymorphism in Glycoprotein-Ibα, a history of obesity, a body mass index, and a history of a previous coronary event.

15. The method of claim 14, wherein the previous coronary event comprises a malignant arrhythmia, a myocardial infarction, and/or an episode of unstable angina.

16. The method of claim 1, wherein the indicator is associated with a p22phox subunit of NAD(P)H oxidase.

17. The method of claim 16, wherein the p22phox subunit of the NAD(P)H oxidase is associated with a genetic polymorphism in the p22phox subunit of the NAD(P)H oxidase.

18. The method of claim 17, wherein the genetic polymorphism comprises a C or T nucleotide at position +242 of the NAD(P)H oxidase gene p22phox subunit.

19. The method of claim 18, wherein the polymorphism further comprises a homozygosity for a C nucleotide at position +242 of the NAD(P)H oxidase gene p22phox subunit.

20. The method of claim 16, wherein the indicator is associated with a presence of the p22phox subunit of the NAD(P)H oxidase detected by genotyping using a melting curve analysis.

21. The method of claim 1, wherein the HDL comprises $H_{2a}$ HDL.

22. The method of claim 1, wherein the HDL comprises an HDL sub-fraction comprising particles corresponding in size to $H_{2a}$ HDL particles.

23. The method of claim 1, wherein the HDL level comprises a serum HDL level and the n risk-factor parameters further include a total serum cholesterol level.

24. The method of claim 1, wherein the risk-factor parameters further comprise a history of a prior myocardial infarction.

25. The method of claim 1, wherein the risk-factor parameters further comprise a body fluid glucose level and a serum triglyceride level.

26. The method of claim 25, wherein the body fluid comprises serum and/or cerebrospinal fluid.

27. The method of claim 1, wherein the risk-factor parameters further comprise a body mass index and a fibrinogen level.

28. The method of claim 1, wherein the risk-factor parameters further comprise a plasminogen activator inhibitor level.

29. The method of claim 28, wherein plasminogen activator inhibitor comprises plasminogen activator inhibitor-1 (PAI-1).

30. The method of claim 1, wherein the risk-factor parameters further comprise a history of metabolic syndrome.

31. The method of claim 1, wherein the risk-factor parameters further comprise a polymorphism in Glycoprotein-Ibα such that there is a threonine or a methionine residue at amino acid residue 145 of Glycoprotein-Ibα.

32. The method of claim 31, wherein the polymorphism comprises at least one Glycoprotein-Ibα allele that encodes a Met at amino acid residue 145.

33. The method of claim 1, wherein the risk-factor parameters further comprise a history of diabetes.

34. The method of claim 1, wherein the risk-factor parameters further comprise a triglyceride level.

35. The method of claim 1, wherein the risk-factor parameters further comprise a lipoprotein-associated phospholipase $A_2$ level.

36. The method of claim 1, wherein at least one of the risk-factor parameters comprises a ranking of values.

37. A method for estimating risk of a coronary event in a subpopulation of patients, comprising:

providing a first plurality of reference data points representing a population of patients, each reference data point representing an (n+1)-dimensional vector comprising a value for each of n risk-factor parameters, wherein n≥2;

wherein each reference data point further comprises a corresponding outcome value; and wherein the outcome value is determined by the prior occurrence or non-occurrence of a coronary event;

mapping each reference data point as a map point in a (n+1)-dimensional space, thereby producing a reference map;
   wherein the position of each map point in n dimensions is determined by the values of the associated reference point's n risk-factor parameters; and
   wherein the position of each map point in the (n+1)th dimension is determined by the outcome value in the associated reference data point;
applying, using a processor, an interpolation algorithm to the reference map to produce an interpolated (n+1)-dimensional map;
   wherein the interpolated (n+1)-dimensional map comprises a surface that defines a function, the function mapping values for the n risk-factor parameters to predicted outcome values; and
   wherein each of the predicted outcome values represents a relative risk and/or a probability of occurrence of the coronary event;
locating on the interpolated (n+1)-dimensional map a first subpopulation of reference data points corresponding to a first subpopulation of patients within the population of patients, the first subpopulation of reference data points representing an increased or decreased risk of the coronary event relative to another subpopulation of patients within the population;
providing a plurality of subpopulation data points corresponding to the first subpopulation of patients, each subpopulation data point comprising a value for each of m risk-factor parameters, wherein m≥2;
   wherein the m risk-factor parameters comprise an HDL level and a C-reactive protein (CRP) level;
   wherein each subpopulation data point further comprises a corresponding subpopulation outcome value; and
   wherein the subpopulation outcome value is determined by the prior occurrence or non-occurrence of the coronary event;
mapping each subpopulation data point as a map point in a (m+1)-dimensional space, thereby producing a second reference map;
   wherein the position of each map point in m dimensions is determined by the values of the associated subpopulation data point's m risk-factor parameters; and
   wherein the position of each map point in the (m+1)th dimension is determined by the subpopulation outcome value for the associated subpopulation data point;
applying an interpolation algorithm to the second reference map to produce an interpolated (m+1)-dimensional map;
   wherein the interpolated (m+1)-dimensional map comprises a second surface that defines a second function that maps values for the m risk-factor parameters to subpopulation predicted outcome values; and
   wherein each of the subpopulation predicted outcome values, as determined by the HDL level and the CRP level, represents a subpopulation relative risk and/or a subpopulation probability of occurrence of the coronary event; and
outputting to an output device, an indicator based on one of the subpopulation predicted outcome values; wherein the indicator indicates that when the person's HDL level is greater than 1 mmol/L, and given the person's CRP level, (a) an HDL level greater than the person's HDL level presents an increased risk of a coronary event; or (b) an HDL level lower than the person's HDL level presents a decreased risk of a coronary event.

\* \* \* \* \*